(12) United States Patent
Pfotenhauer et al.

(10) Patent No.: US 11,882,991 B2
(45) Date of Patent: *Jan. 30, 2024

(54) TORQUE-LIMITING DEVICES, SYSTEMS, AND METHODS

(71) Applicant: Pro-Dex, Inc., Irvine, CA (US)

(72) Inventors: Alexander M. Pfotenhauer, Tustin, CA (US); Manouchehr Goharlaee, Irvine, CA (US)

(73) Assignee: Pro-Dex, Inc., Irvine, CA (US)

( * ) Notice: Subject to any disclaimer, the term of this patent is extended or adjusted under 35 U.S.C. 154(b) by 371 days.

This patent is subject to a terminal disclaimer.

(21) Appl. No.: 17/371,760

(22) Filed: Jul. 9, 2021

(65) Prior Publication Data

US 2022/0202521 A1 Jun. 30, 2022

Related U.S. Application Data

(63) Continuation of application No. 16/544,512, filed on Aug. 19, 2019, now Pat. No. 11,090,128.

(60) Provisional application No. 62/719,874, filed on Aug. 20, 2018.

(51) Int. Cl.
*A61B 90/00* (2016.01)
*A61B 17/16* (2006.01)

(52) U.S. Cl.
CPC .......... *A61B 90/03* (2016.02); *A61B 17/1626* (2013.01); *A61B 17/1628* (2013.01); *A61B 2090/031* (2016.02); *A61B 2090/066* (2016.02)

(58) Field of Classification Search
CPC .............................. A61B 90/03; A61B 17/1626
See application file for complete search history.

(56) References Cited

U.S. PATENT DOCUMENTS

| 2,414,882 A | 1/1947 | Longfellow |
| 2,979,089 A | 4/1961 | Piesker |
| 3,120,845 A | 2/1964 | Horner |
| 3,578,872 A | 5/1971 | McBurnie |
| 3,643,501 A | 2/1972 | Pauley |
| 3,692,910 A | 9/1972 | Laguzzi |

(Continued)

FOREIGN PATENT DOCUMENTS

| CN | 105491965 A | 4/2016 |
| DE | 2010914 A1 | 9/1971 |

(Continued)

OTHER PUBLICATIONS

Boys, J.T., "Design and Performance of an Automatic Control System for Fastener Tightening," Applied Mechanics Group, vol. 191, Issue 1, Jun. 1, 1977, in 11 pages.

(Continued)

*Primary Examiner* — Christian A Sevilla
(74) *Attorney, Agent, or Firm* — Knobbe, Martens, Olson & Bear, LLP

(57) ABSTRACT

Various torque-limiting surgical driver devices, systems, and methods are disclosed. The surgical driver can include a body, a motor that is configured to rotate a drill bit engaged with the surgical driver, and a processor configured to control operation of the surgical driver. The surgical driver can have torque-limiting functionality, such as by monitoring the amount of torque applied to a drill bit and reducing or stopping rotation of the drill bit when certain torque-limiting criteria are met.

17 Claims, 12 Drawing Sheets

(56) References Cited

U.S. PATENT DOCUMENTS

| | | |
|---|---|---|
| 3,926,264 A | 12/1975 | Bardwell et al. |
| 3,962,910 A | 6/1976 | Spyridakis et al. |
| 3,973,434 A | 8/1976 | Smith |
| 3,974,685 A | 8/1976 | Walker |
| 3,974,883 A | 8/1976 | Sigmund |
| 3,982,419 A | 9/1976 | Boys |
| 4,008,772 A | 2/1977 | Boys |
| 4,008,773 A | 2/1977 | Wallace et al. |
| 4,013,895 A | 3/1977 | Akiyoshi et al. |
| 4,023,406 A | 5/1977 | Benz, Jr. |
| 4,078,589 A | 3/1978 | Miller |
| 4,081,037 A | 3/1978 | Jonsson |
| 4,095,325 A | 6/1978 | Hashimoto et al. |
| 4,102,182 A | 7/1978 | Brown et al. |
| 4,104,778 A | 8/1978 | Vliet |
| 4,104,780 A | 8/1978 | Sigmund |
| 4,106,176 A | 8/1978 | Rice et al. |
| 4,110,829 A | 8/1978 | Boys |
| 4,163,310 A | 8/1979 | Sigmund |
| 4,179,786 A | 12/1979 | Eshghy |
| 4,233,721 A | 11/1980 | Eshghy |
| 4,244,213 A | 1/1981 | Marcinkiewicz |
| 4,249,117 A | 2/1981 | Leukhardt et al. |
| 4,267,914 A | 5/1981 | Saar |
| 4,273,198 A | 6/1981 | Doniwa |
| 4,292,571 A | 9/1981 | Cuneo |
| 4,344,216 A | 8/1982 | Finkelston |
| 4,359,906 A | 11/1982 | Cordey |
| 4,361,945 A | 12/1982 | Eshghy |
| 4,375,120 A | 3/1983 | Sigmund |
| 4,375,121 A | 3/1983 | Sigmund |
| 4,375,122 A | 3/1983 | Sigmund |
| 4,375,123 A | 3/1983 | Ney |
| 4,426,588 A | 1/1984 | Weilenmann |
| RE31,569 E | 5/1984 | Eshghy |
| 4,450,727 A | 5/1984 | Reinholm et al. |
| 4,562,389 A | 12/1985 | Jundt et al. |
| 4,684,922 A | 8/1987 | Minogue |
| 4,705,038 A | 11/1987 | Sjostrom et al. |
| 4,721,169 A | 1/1988 | Nagasawa et al. |
| 4,830,549 A | 5/1989 | Neumaier et al. |
| 4,878,404 A | 11/1989 | Liao |
| 4,894,767 A | 1/1990 | Doniwa |
| 4,908,926 A | 3/1990 | Takeshima et al. |
| 4,995,877 A | 2/1991 | Ams et al. |
| 5,014,793 A | 5/1991 | Germanton |
| 5,038,084 A | 8/1991 | Wing |
| 5,061,885 A | 10/1991 | Fukuhara |
| 5,131,130 A | 7/1992 | Eshghy |
| 5,152,046 A | 10/1992 | Abe |
| 5,154,242 A | 10/1992 | Soshin et al. |
| 5,155,421 A | 10/1992 | Hansson |
| 5,160,978 A | 11/1992 | Faville |
| 5,207,697 A | 5/1993 | Carusillo et al. |
| 5,284,217 A | 2/1994 | Eshghy |
| RE34,556 E | 3/1994 | Sjostrom et al. |
| 5,315,501 A | 5/1994 | Whitehouse |
| 5,337,638 A | 8/1994 | Coss |
| 5,382,251 A | 1/1995 | Hood et al. |
| 5,404,643 A | 4/1995 | Rice |
| 5,410,229 A | 4/1995 | Sebastian et al. |
| 5,430,923 A | 7/1995 | Parent et al. |
| 5,440,215 A | 8/1995 | Gilmore |
| 5,496,330 A | 3/1996 | Bates et al. |
| 5,536,267 A | 7/1996 | Edwards et al. |
| 5,538,423 A | 7/1996 | Coss et al. |
| 5,539,288 A | 7/1996 | Neijzen et al. |
| 5,543,695 A | 8/1996 | Culp et al. |
| 5,563,482 A | 10/1996 | Shaw et al. |
| 5,584,619 A | 10/1996 | Guzzella |
| 5,591,919 A | 1/1997 | Hathaway et al. |
| 5,626,474 A | 1/1997 | Kukla et al. |
| 5,632,759 A | 5/1997 | Rexroth |
| 5,637,968 A | 6/1997 | Kainec et al. |
| 5,689,159 A | 11/1997 | Culp et al. |
| 5,725,533 A | 3/1998 | Carlsson |
| 5,731,673 A | 3/1998 | Gilmore |
| 5,754,019 A | 5/1998 | Walz |
| 5,810,821 A | 9/1998 | Vandewalle |
| 5,831,404 A | 11/1998 | Ishii |
| 5,868,746 A | 2/1999 | Sarver et al. |
| 5,874,816 A | 2/1999 | Ishii |
| 5,890,405 A | 4/1999 | Becker |
| 5,898,112 A | 4/1999 | Dawood |
| 5,904,689 A | 5/1999 | Jonjic |
| 5,927,976 A | 7/1999 | Wu |
| 5,980,248 A | 11/1999 | Kusakabe et al. |
| 5,993,454 A | 11/1999 | Longo |
| 6,022,352 A | 2/2000 | Vandewalle |
| 6,084,366 A | 7/2000 | Koselke et al. |
| 6,110,174 A | 8/2000 | Nichter |
| 6,132,435 A * | 10/2000 | Young ................ A61B 17/8875 464/36 |
| 6,162,053 A | 12/2000 | Hollander |
| 6,171,312 B1 | 1/2001 | Beaty |
| 6,179,841 B1 | 1/2001 | Jackson |
| 6,197,065 B1 | 3/2001 | Martin et al. |
| 6,211,636 B1 | 4/2001 | Matsubara et al. |
| 6,257,351 B1 | 7/2001 | Ark et al. |
| 6,280,476 B1 | 8/2001 | Metzger et al. |
| RE37,358 E | 9/2001 | Del Rio et al. |
| 6,329,778 B1 | 12/2001 | Culp et al. |
| 6,378,623 B2 | 4/2002 | Kawarai |
| 6,402,757 B1 | 6/2002 | Moore, III et al. |
| 6,471,707 B1 | 10/2002 | Miller et al. |
| 6,479,958 B1 | 11/2002 | Thompson et al. |
| 6,500,208 B1 | 12/2002 | Metzger et al. |
| 6,508,841 B2 | 1/2003 | Martin et al. |
| 6,516,896 B1 | 2/2003 | Bookshar et al. |
| 6,536,536 B1 | 3/2003 | Gass et al. |
| 6,537,274 B1 | 3/2003 | Katz |
| 6,547,565 B1 | 4/2003 | Dawood et al. |
| 6,569,186 B1 | 5/2003 | Winters et al. |
| 6,607,385 B1 | 8/2003 | Sevcik et al. |
| 6,616,446 B1 | 9/2003 | Schmid |
| 6,629,778 B1 | 10/2003 | Enderle et al. |
| 6,656,184 B1 | 12/2003 | White et al. |
| 6,665,948 B1 * | 12/2003 | Kozin ................... A61B 90/06 175/45 |
| 6,676,665 B2 | 1/2004 | Foley et al. |
| 6,680,595 B2 | 1/2004 | Ito |
| 6,700,341 B2 | 3/2004 | Schaer et al. |
| 6,712,855 B2 | 3/2004 | Martin et al. |
| 6,723,099 B1 | 4/2004 | Goshert |
| 6,780,175 B1 | 8/2004 | Sachdeva et al. |
| 6,916,340 B2 | 7/2005 | Metzger et al. |
| 6,923,813 B2 | 8/2005 | Phillips et al. |
| 6,954,682 B2 | 10/2005 | Makimae et al. |
| 6,981,976 B1 | 1/2006 | Schoenefeld |
| 7,062,979 B2 | 6/2006 | Day et al. |
| 7,091,683 B1 | 8/2006 | Smith et al. |
| 7,141,073 B2 | 11/2006 | May et al. |
| 7,185,562 B2 | 3/2007 | Raines, Jr. et al. |
| 7,234,536 B2 | 6/2007 | Scholl et al. |
| 7,235,940 B2 | 6/2007 | Bosch et al. |
| 7,250,055 B1 | 7/2007 | Vanderwalle |
| 7,255,703 B2 | 8/2007 | Mujwid et al. |
| 7,306,607 B2 | 12/2007 | Metzger |
| 7,331,406 B2 | 2/2008 | Wottreng, Jr. et al. |
| 7,335,207 B1 | 2/2008 | Smith |
| 7,338,286 B2 | 3/2008 | Porter et al. |
| 7,344,376 B2 | 3/2008 | Beaty et al. |
| 7,398,700 B2 | 7/2008 | Makimae et al. |
| 7,400,106 B2 | 7/2008 | DeCicco et al. |
| 7,431,682 B2 | 10/2008 | Zeiler et al. |
| 7,435,085 B2 | 10/2008 | Gugel et al. |
| 7,441,480 B2 | 10/2008 | Raines, Jr. et al. |
| 7,481,832 B1 | 1/2009 | Meridew et al. |
| 7,484,959 B2 | 2/2009 | Porter et al. |
| 7,488,323 B2 | 2/2009 | Bacastow et al. |
| 7,507,231 B2 | 3/2009 | Schmieding et al. |
| 7,604,636 B1 | 10/2009 | Walters et al. |
| 7,713,285 B1 | 5/2010 | Stone et al. |
| 7,722,678 B2 | 5/2010 | Brown et al. |

(56) References Cited

U.S. PATENT DOCUMENTS

| | | |
|---|---|---|
| 7,727,282 B2 | 6/2010 | Slone et al. |
| 7,740,425 B2 | 6/2010 | Zeiler et al. |
| 7,770,658 B2 | 8/2010 | Ito et al. |
| 7,823,465 B2 | 11/2010 | Makimae et al. |
| 7,839,112 B2 | 11/2010 | Wei |
| 7,849,766 B2 | 12/2010 | Sharifi-Mehr et al. |
| 7,850,452 B2 | 12/2010 | Suttin et al. |
| 7,881,806 B2 | 2/2011 | Horrigan et al. |
| 7,887,559 B2 | 2/2011 | Deng et al. |
| 7,896,923 B2 | 3/2011 | Blackwell et al. |
| 7,936,140 B2 | 5/2011 | Wei |
| 7,955,334 B2 | 6/2011 | Steiner et al. |
| 8,012,215 B2 | 9/2011 | Metzger et al. |
| 8,025,106 B2 | 9/2011 | Schmidt |
| 8,028,608 B2 | 10/2011 | Sixto, Jr. et al. |
| 8,035,487 B2 | 10/2011 | Malackowski |
| 8,038,702 B2 | 10/2011 | Yuan et al. |
| 8,048,115 B2 | 11/2011 | Winslow et al. |
| 8,057,538 B2 | 11/2011 | Bergin et al. |
| 8,074,334 B2 | 12/2011 | Tharp et al. |
| 8,083,596 B1 | 12/2011 | Silver et al. |
| 8,087,935 B2 | 1/2012 | Beaty et al. |
| 8,103,358 B2 | 1/2012 | Sommer et al. |
| 8,136,431 B2 | 3/2012 | Wengreen |
| 8,147,498 B2 | 4/2012 | Schlueter et al. |
| 8,161,613 B2 | 4/2012 | Schuele et al. |
| 8,172,004 B2 | 5/2012 | Ho |
| 8,182,539 B2 | 5/2012 | Tyber et al. |
| 8,276,487 B2 | 10/2012 | Wengreen et al. |
| 8,286,723 B2 | 10/2012 | Puzio et al. |
| 8,322,456 B2 | 12/2012 | Pozgay et al. |
| 8,347,768 B2 | 1/2013 | Witte |
| 8,372,085 B2 | 2/2013 | Prager et al. |
| 8,425,521 B2 | 4/2013 | Cremer et al. |
| 8,463,421 B2 | 6/2013 | Brett et al. |
| 8,485,075 B1 | 7/2013 | Gauthier et al. |
| 8,523,845 B2 | 9/2013 | Ippisch |
| 8,529,567 B2 | 9/2013 | Garcia et al. |
| 8,603,148 B2 | 12/2013 | Raven, III et al. |
| 8,821,493 B2 | 9/2014 | Anderson |
| 8,894,654 B2 | 11/2014 | Anderson |
| D719,594 S | 12/2014 | Leugers |
| D722,627 S | 2/2015 | Leugers |
| D727,985 S | 4/2015 | Leugers |
| D732,364 S | 6/2015 | Rinaldis et al. |
| 9,204,885 B2 | 12/2015 | McGinley et al. |
| 9,265,551 B2 | 2/2016 | Kust et al. |
| 9,277,926 B2 | 3/2016 | Xu et al. |
| D759,244 S | 6/2016 | Leugers |
| D759,245 S | 6/2016 | Leugers |
| 9,358,016 B2 | 6/2016 | McGinley et al. |
| 9,370,372 B2 | 6/2016 | McGinley et al. |
| 9,468,445 B2 | 10/2016 | McGinley et al. |
| 9,468,978 B2 | 10/2016 | Lo et al. |
| 9,492,181 B2 | 11/2016 | McGinley et al. |
| 9,554,807 B2 | 1/2017 | McGinley et al. |
| 9,554,812 B2 | 1/2017 | Inkpen et al. |
| 9,561,544 B2 | 2/2017 | Walsh et al. |
| 9,585,677 B2 | 3/2017 | Garcia et al. |
| 9,649,141 B2 | 5/2017 | Raven, III et al. |
| D791,944 S | 7/2017 | Palazzolo et al. |
| D793,831 S | 8/2017 | Russell et al. |
| D793,832 S | 8/2017 | Russell et al. |
| D793,833 S | 8/2017 | Russell et al. |
| D794,190 S | 8/2017 | Russell et al. |
| D794,196 S | 8/2017 | Russell et al. |
| 9,826,984 B2 | 11/2017 | McGinley et al. |
| 9,833,244 B2 | 12/2017 | McGinley et al. |
| 9,833,270 B2 | 12/2017 | Zlotolow |
| 9,877,734 B2 | 1/2018 | Anderson |
| 10,028,801 B1 | 7/2018 | McGinley et al. |
| 10,111,688 B2 | 10/2018 | Raven, III et al. |
| 10,117,689 B2 | 11/2018 | Zlotolow |
| 10,149,686 B2 | 12/2018 | Anderson |
| 10,206,731 B2 | 2/2019 | Kust et al. |
| 10,383,674 B2 | 8/2019 | Sexson et al. |
| 11,071,575 B2 | 7/2021 | Sexson et al. |
| 11,090,128 B2 | 8/2021 | Pfotenhauer et al. |
| 2002/0146663 A1 | 10/2002 | Nakanishi et al. |
| 2003/0093103 A1 | 5/2003 | Malackowski et al. |
| 2003/0121685 A1 | 7/2003 | Yamamoto |
| 2003/0173096 A1 | 9/2003 | Setton et al. |
| 2004/0024311 A1* | 2/2004 | Quaid, III ............ A61B 90/36 |
| | | 600/428 |
| 2005/0096684 A1 | 5/2005 | Farrow et al. |
| 2005/0116673 A1* | 6/2005 | Carl ................ A61B 17/1626 |
| | | 318/432 |
| 2005/0131415 A1* | 6/2005 | Hearn ................ B25B 23/147 |
| | | 606/80 |
| 2005/0205274 A1 | 9/2005 | Bogue |
| 2005/0268750 A1* | 12/2005 | Bruce ................ B25B 21/002 |
| | | 81/52 |
| 2006/0117911 A1 | 6/2006 | Raines, Jr. et al. |
| 2006/0234617 A1 | 10/2006 | Francis et al. |
| 2007/0060933 A1 | 3/2007 | Sankaran et al. |
| 2007/0085496 A1 | 4/2007 | Philipp et al. |
| 2007/0125201 A1 | 6/2007 | Raines et al. |
| 2007/0141110 A1 | 6/2007 | Stone et al. |
| 2007/0179476 A1 | 8/2007 | Shelton et al. |
| 2007/0191915 A1 | 8/2007 | Strother et al. |
| 2007/0256527 A1* | 11/2007 | Phan ................ B25B 23/1427 |
| | | 81/475 |
| 2008/0004646 A1 | 1/2008 | To et al. |
| 2008/0016990 A1 | 1/2008 | Rinner |
| 2008/0060487 A1 | 3/2008 | Schell |
| 2008/0133020 A1 | 6/2008 | Blackwell et al. |
| 2008/0153062 A1 | 6/2008 | Beaty et al. |
| 2008/0215060 A1 | 9/2008 | Garcia et al. |
| 2008/0221564 A1 | 9/2008 | Rouiller et al. |
| 2008/0286722 A1 | 11/2008 | Berckmans, III et al. |
| 2009/0014192 A1 | 1/2009 | Ito et al. |
| 2009/0260485 A1 | 10/2009 | Hohmann et al. |
| 2010/0034605 A1 | 2/2010 | Huckins et al. |
| 2010/0063508 A1 | 3/2010 | Borja et al. |
| 2010/0116519 A1 | 5/2010 | Gareis |
| 2010/0204685 A1 | 8/2010 | Ippisch |
| 2010/0222812 A1 | 9/2010 | Stone et al. |
| 2010/0318093 A1 | 12/2010 | Ippisch |
| 2011/0000688 A1 | 1/2011 | Iwata |
| 2011/0190907 A1 | 8/2011 | Porter et al. |
| 2011/0245833 A1 | 10/2011 | Anderson |
| 2011/0288549 A1 | 11/2011 | Steiner et al. |
| 2011/0301611 A1 | 12/2011 | Garcia et al. |
| 2011/0306008 A1 | 12/2011 | Suttin et al. |
| 2011/0306009 A1 | 12/2011 | Suttin et al. |
| 2011/0319745 A1 | 12/2011 | Frey |
| 2012/0046665 A1 | 2/2012 | Kim |
| 2012/0067139 A1 | 3/2012 | Pernestal |
| 2012/0116494 A1 | 5/2012 | Leynov et al. |
| 2012/0184958 A1 | 7/2012 | Knuchel et al. |
| 2012/0255756 A1 | 10/2012 | Aoki |
| 2013/0014368 A1 | 1/2013 | Woods et al. |
| 2013/0025892 A1 | 1/2013 | Mashiko et al. |
| 2013/0098646 A1 | 4/2013 | Funabashi et al. |
| 2013/0105189 A1 | 5/2013 | Murthy et al. |
| 2013/0116519 A1 | 5/2013 | Wood |
| 2013/0118323 A1 | 5/2013 | Witte |
| 2013/0165930 A1 | 6/2013 | Lehmann et al. |
| 2013/0193891 A1 | 8/2013 | Wood et al. |
| 2013/0269961 A1 | 10/2013 | Lim et al. |
| 2013/0319190 A1 | 12/2013 | Nino et al. |
| 2013/0327552 A1 | 12/2013 | Lovelass et al. |
| 2013/0331895 A1 | 12/2013 | Garcia et al. |
| 2013/0331994 A1 | 12/2013 | Ng et al. |
| 2013/0341058 A1 | 12/2013 | Roehm |
| 2014/0048298 A1 | 2/2014 | Fuchs |
| 2014/0296845 A1 | 10/2014 | Miller et al. |
| 2015/0025538 A1* | 1/2015 | Kust ................ B25B 23/147 |
| | | 606/104 |
| 2015/0066036 A1 | 3/2015 | McGinley et al. |
| 2015/0182285 A1 | 7/2015 | Yen et al. |
| 2015/0201918 A1 | 7/2015 | Kumar et al. |
| 2016/0128704 A1 | 5/2016 | McGinley et al. |
| 2016/0206328 A1 | 7/2016 | Lo et al. |

(56) References Cited

U.S. PATENT DOCUMENTS

| | | |
|---|---|---|
| 2016/0256213 A1 | 9/2016 | Kust et al. |
| 2017/0007289 A1 | 1/2017 | McGinley et al. |
| 2017/0128081 A1 | 5/2017 | McGinley |
| 2017/0143396 A1 | 5/2017 | McGinley et al. |
| 2017/0143440 A1 | 5/2017 | McGinley et al. |
| 2017/0181758 A1 | 6/2017 | Brotman |
| 2017/0189037 A1 | 7/2017 | McGinley et al. |
| 2017/0296250 A1 | 10/2017 | McGinley et al. |
| 2017/0348037 A1 | 12/2017 | Sexson et al. |
| 2018/0185034 A1 | 7/2018 | McGinley et al. |
| 2019/0013830 A1 | 1/2019 | Hoglund et al. |
| 2019/0029697 A1 | 1/2019 | Anderson et al. |
| 2020/0038085 A1 | 2/2020 | Sexson et al. |
| 2020/0054410 A1 | 2/2020 | Pfotenhauer et al. |
| 2021/0085342 A1* | 3/2021 | Ayer .................. B23B 49/00 |
| 2021/0378726 A1 | 12/2021 | Sexson et al. |

FOREIGN PATENT DOCUMENTS

| | | |
|---|---|---|
| DE | 3238069 A1 | 4/1984 |
| DE | 19620782 A1 | 12/1996 |
| DE | 19845871 | 4/1999 |
| EP | 0170068 A2 | 2/1986 |
| JP | S52-46600 | 4/1977 |
| JP | S63-150167 A | 6/1988 |
| JP | H06-210575 A | 8/1994 |
| JP | H07-124827 A | 5/1995 |
| JP | H07-256566 A | 10/1995 |
| JP | H08-281567 | 10/1996 |
| JP | 2959294 | 7/1999 |
| JP | 2002-283248 | 10/2002 |
| JP | 2005-066787 A | 3/2005 |
| JP | 2005-118911 A | 5/2005 |
| JP | 2005-523174 A | 8/2005 |
| JP | 2009-125907 A | 6/2009 |
| JP | 2012-200807 A | 10/2012 |
| JP | 2004-291143 | 12/2016 |
| WO | WO 03/090974 A1 | 11/2003 |
| WO | WO 03/101322 A1 | 12/2003 |
| WO | WO 2004/110293 A1 | 12/2004 |
| WO | WO 2008/105057 A1 | 9/2008 |
| WO | WO 2008/128523 A2 | 10/2008 |
| WO | WO 2011/133160 A1 | 10/2011 |
| WO | WO 2012/109760 | 8/2012 |
| WO | WO 2015/006296 | 1/2015 |
| WO | WO 2015/009850 A1 | 1/2015 |
| WO | WO 2017/083992 A1 | 5/2017 |
| WO | WO 2017/139674 A1 | 8/2017 |
| WO | WO 2017/214194 A1 | 12/2017 |
| WO | WO 2018/132835 A1 | 7/2018 |
| WO | WO 2020/041211 A1 | 2/2020 |

OTHER PUBLICATIONS

International Preliminary Report on Patentability from corresponding International Application No. PCT/US2019/047089, dated Mar. 4, 2021, 8 pages.

Office Action from corresponding Chinese Patent Application No. 201980052230.3, dated Mar. 2, 2022, 14 pages.

Extended European Search Report received in Application No. 19851881.3, dated Mar. 23, 2022, in 7 pages.

Brockwell, P., Excerpt from Introduction to Time Series and Forecasting, 2d Ed., 2002.

Brown, R.G., Excerpt from Smoothing, Forecasting and Prediction of Discrete Time Series, 1963.

Gill, P.J., The Yielding of Fastenings During Tightening, The Japan Research Institute, vol. 7, No. 12., 1976.

Hatcher, "Evaluation of the iQTM Intelligent System for Rapid Screw Insertion," undated but believed to be publicly available at least as early as Dec. 2012 (e.g., via http://pharma-gate.net/wp content/uploads/ 2012/12/1.pdf).

Hsu, et al., A Modular Mechatronic System for Automatic Bone Drilling, Biomedical Engineering Applications, Basis, & Communications, vol. 13, No. 4, Aug. 2001.

https://cwisociety.org/wp-content/uploads/2020/04/MatrixRIB_CWIS-Full_Page_Ad-1.pdf, "The Perfect Combination", retrieved May 25, 2020, 1 page.

https://patents.google.com/patent/US20070256527, "Torque limiting device and methods", retrieved on Feb. 9, 2021, 7 pages.

https://patents.google.com/patent/US6132435A/en, "Torque limiting device for surgical use", retrieved Feb. 9, 2021, 12 pages.

https://www.hospimedica.com/surgical-techniques/articles/294743226/novel-torque-limiting-instruments-for-orthopedic-surgeons.html, "Novel Torque Limiting Instruments for Orthopedic Surgeons", posted Nov. 5, 2012, retrieved Dec. 6, 2020, 3 pages.

https://www.medicaldesignandoutsourcing.com/torque-fast-series-of-disposable-surgical-instruments-launched/, "Torque Fast Series of Disposable Surgical Instruments Launched", posted Oct. 8, 2013, retrieved Dec. 7, 2020, 3 pages.

https://www.odtmag.com/contents/view_features/2007-12-05/applying-reliability-concepts-to-torque-limit/, "Applying Reliability Concepts to Torque-Limiting Instruments", retrieved Feb. 9, 2021, 6 pages.

https://www.portescap.com/en/industries-supported/surgical-power-tools/powered-surgical-screwdrivers, "Miniature Motors for Powered Surgical Screwdrivers", retrieved on Feb. 9, 2021, 3 pages.

https://www.pro-dex.com/turnkey-solutions, Pro-Dex, retrieved May 25, 2020, 2 pages.

International Search Report and Written Opinion from corresponding International Application No. PCT/US2017/036216, dated Oct. 10, 2017, 12 pages.

Search Report and Written Opinion in International Application No. PCT/US2019/047089, dated Oct. 16, 2019, in 19 pages.

Sears/Zemansky/Young, Excerpt from "University Physics," 1986.

Smith, S., Excerpt from "The Scientist and Engineer's Guide to Digital Signal Processing," 2d Ed. 1999.

Wadsworth, H., Excerpt from Handbook of Statistical Methods for Engineers and Scientists, 2d Ed., 1990.

* cited by examiner

TORQUE-LIMITING DEVICES, SYSTEMS, AND METHODS

CROSS REFERENCE

This application is a continuation of U.S. application Ser. No. 16/544,512, filed Aug. 19, 2019, and titled "TORQUE-LIMITING DEVICES, SYSTEMS, AND METHODS," which claims from the benefit of U.S. Provisional Application No. 62/719,874, filed Aug. 20, 2018, and titled "TORQUE-LIMITING DRILLING." The entirety of each of the aforementioned applications is incorporated by reference herein.

BACKGROUND

Field

This disclosure generally relates to torque-limiting surgical driver devices, systems, and methods, such as torque-limiting surgical drivers for use in orthopedic surgeries.

Certain Related Art

In certain surgical procedures, medical professionals (for example, surgeons) utilize hand-powered instruments to drill into a bone of a patient. As powered surgical instruments have become more commonplace, medical professionals have moved away from manual surgical drilling instruments and methods when drilling and driving into patient bone. Powered surgical instruments operate at much higher speeds than hand-actuated, manual surgical instruments. However, while such powered instruments provide many benefits, it is difficult for medical professionals to determine when a drill bit has transitioned through different layers of the bones and/or when a drill bit has penetrated through the entirety of the bone cross-section.

SUMMARY OF CERTAIN FEATURES

It can be beneficial to detect when a surgical drill is presently drilling through particular layers of bone, transitions between different layers of the bone, and/or has penetrated through an entirety of a cross-section of bone. Such detection can avoid or reduce potential damage to tissue proximate to a patient's bone, such as tissue or nearby organs. For example, it can be beneficial for a surgical drill to differentiate between varying densities of bone in order to provide continuous feedback as to the current location of a drill bit within the bone. Such "tissue differentiation" or "density differentiation" can help avoid "plunging" of the drill bit through and/or outside the bone which can cause damage to tissue proximate or adjacent the bone. This can be accomplished with a surgical driver that monitors the torque applied to the drill bit and stops or reduces the rotation of the drill bit when certain torque criteria are satisfied. For example, the criteria can include the amount of torque being applied, how the torque is changing over time (e.g., whether the torque is consistently or inconsistently increasing or decreasing), how current torque values compare with previously-measured torque values and/or thresholds. Certain comparisons or thresholds of measured torque values can aid in determining whether present or recent torque values being sensed are indicative of the drill bit being located (or drilling through) a harder portion of the bone, which can in turn indicate that the drill bit is about to exit the bone cross-section. Additionally or alternatively, certain comparisons or thresholds of measured torque values can aid in determining whether present or recent torque values being sensed indicate that the drill bit has breached the bone. As discussed further below, the surgical driver can detect whether the drill bit is drilling through, or has drilled through, the harder (cortical) portion of the bone around the softer (cancellous) portion of the bone, and/or whether the drill bit has drilled through one or both of the entry and exit portions of the harder (cortical) portion. Some embodiments are configured to detect that the drill bit has passed through a softer tissue and then to stop upon, or soon after, encountering and/or beginning to drill into a harder tissue. For example, to detect that the drill bit has passed through a spinal disk and is at a vertebrae. Certain embodiments operate with algorithms such as those described herein, but without those steps that relate to and/or are dependent on detecting a first cortical layer of bone.

Various surgical drivers and associated systems and methods are disclosed that address one or more of the concerns discussed above, or other concerns. Embodiments of the surgical drivers, systems, and methods can be used for many different procedures, such as reconstructive, clavicle, craniomaxillofacial, thoracic, spinal, fracture repair, and extremity surgical approaches, among others. Further, in the reconstructive process, embodiments can be used for joint replacements (such as for patients suffering from arthritis), reconstructive orthopedics can restore the function of joints by replacing them. This can include knee, hip, and shoulder surgeries, though other surgeries can be used as well. Fracture repair can be used with respect to bones experiencing trauma, such as large bones like the femur. Further, extremities can be reconstructive, which can include joints such as ankles, writs, hands, fingers, feet, and toes. Each of the determined torque values can vary depending on the particular application, such as those discussed above. Embodiments can be used in the orthopedic realm and outside the orthopedic realm.

Some embodiments are configured to identify differentiations in torque characteristics. In some embodiments, the surgical driver can differentiate different bodily tissue (e.g., different bone tissues) so that the user will know where they are operating (e.g., where the tip of the drill bit is located). In certain embodiments, the surgical driver is configured to reduce or avoid breaching of a bone (e.g., a clavicle), such as with a drill bit.

The surgical driver can include a body and a motor. The motor can be operably connected to a drive head at a distal end of the surgical driver such that the motor can turn the drive head. The drive head can receive a drill bit. The drill bit can be positioned at a desired drill location on a substrate (e.g., a bone) and the motor can be operated to drive the drill bit into a substrate. Various embodiments of the surgical driver can limit and/or control torque applied to the drill bit. Certain embodiments reduce the speed of the drill bit during the drilling process. Various embodiments provide one or more of the advantages described above, or other advantages.

In some embodiments, a powered device (such as a surgical driver) can be capable of determining torque (e.g., by reading current and/or voltage) and a controller (either inside the device or outside the device) can be configured to implement torque-limiting functionality. In some embodiments, the device can be programmed to use current, voltage, and/or torque values to identify the substrate through which the drill bit is drilling and manage drive velocity accordingly. In some embodiments, the device can be programmed to use current, voltage, and/or torque values to identify changes in the drill bit path through more or less dense materials (such as through harder or softer portions of a bone). In some embodiments, the device can identify cortical and cancellous bone using discrete current, voltage, and/or torque values and can use the values to interpret the current substrate of the drill bit and control the powered device accordingly. For example, some implementations are configured to stop the device if a higher density tissue type is detected, such as a cortical portion of a bone.

Disclosed herein are embodiments of a torque-limiting surgical driver comprising: a body comprising a handle that is configured to be grasped by a user; a motor positioned in the body; a drive head configured to be rotated by the motor and to receive a drill bit; a power source configured to provide electric power to the motor; and a processor positioned in the body. In some embodiments, under the control of the processor, the torque-limiting surgical driver is configured to: apply torque to the drill bit to drill into a bone; monitor current or voltage supplied to the motor; determine, from the current or voltage supplied to the motor, torque values applied to the drill bit as the drill bit drills through the bone; and determine that a torque-limiting condition is satisfied. In some embodiments, the determining that the torque-limiting condition is satisfied comprises: determining that the drill bit has drilled in or through a first cortical layer of the bone; and determining that the drill bit has drilled through a second cortical layer of the bone; and in response to determining that the torque-limiting condition is satisfied, stopping the application of torque to the drill bit.

In some embodiments, the torque-limiting surgical driver is configured to determine whether the drill bit has drilled in or through the first cortical portion of the bone by comparing a difference between a first pair of consecutive torque values to a first threshold. In some embodiments, the torque-limiting surgical driver is configured to determine whether the drill bit has drilled in or through the first cortical portion of the bone by further comparing a difference between a second pair of consecutive torque values to the first threshold. In some embodiments, if the difference between the first pair of consecutive torque values is not greater than or equal to the first threshold, the torque-limiting surgical driver is further configured to compare a difference between a first pair of non-consecutive torque values with a second threshold, wherein the second threshold is greater than the first threshold. In some embodiments, if the difference between the first pair of non-consecutive torque values is not greater than or equal to the second threshold, the torque-limiting surgical driver is further configured to compare a second pair of non-consecutive torque values with the second threshold.

In some embodiments, the torque-limiting surgical driver is further configured to determine at least one of: whether the drill bit has drilled through an entry point of the second cortical portion of the bone; and whether the drill bit is drilling in the second cortical portion of the bone. In some embodiments, the torque-limiting surgical driver is configured to determine whether the drill bit has drilled through the entry point of the second cortical portion of the bone by comparing a difference between a second pair of consecutive torque values to a second threshold, the second pair of consecutive torque values obtained after the first pair of consecutive torque values. In some embodiments, the second threshold is equal to a percentage of an average of a subset of all the determined torque values. In some embodiments, the subset of all of the determined torque values is equal to all of the determined torque values that are greater than or equal to a third threshold, wherein the third threshold is indicative of drilling through a material other than air. In some embodiments, the torque-limiting surgical driver is configured to determine whether the drill bit is drilling in the second cortical portion of the bone by comparing a difference between a current torque value and a maximum measured torque value to a second threshold.

In some embodiments, in response to a determination that the drill bit has drilled through the entry point of the second cortical portion of the bone or a determination that the drill bit is drilling in the second cortical portion of the bone, the torque-limiting surgical driver is further configured to determine an average torque value, the average torque value representative of the torque values measured when the drill bit is drilling in the second cortical portion of the bone. In some embodiments, the torque-limiting surgical driver is further configured to determine a difference between a first torque value and the average torque value, the first torque value being a current torque value measured by the torque-limiting surgical driver.

In some embodiments, the surgical driver is configured to limit the amount of torque applied to the drill bit in response to a determination that the first torque value is less than the average torque value. In some embodiments, the torque-limiting surgical driver is further configured to: determine a difference between a second torque value and the average torque value, the second torque value measured prior to the first torque value; and limit the amount of torque applied to the drill bit in response to a determination that both of the first and second torque values are less than the average torque value.

Disclosed herein are methods of controlling a torque-limiting driver to limit the amount of torque applied to a drill bit after breaching a bone. In some embodiments, the torque-limiting driver comprises a body with a handle, a motor positioned in the body, a drive head that is configured to receive a drill bit and to be rotated by the motor so as to enable the drill bit to drill into the bone, and a processor. In some embodiments, under the control of the processor the method comprises: driving the drill bit into the bone, wherein the bone comprises a first cortical layer, a second cortical layer, and a cancellous layer in between the first and second cortical layers; detecting torque values when the drill bit is drilling into the bone; determining whether the drill bit has drilled in the first cortical layer of the bone; determining whether the drill bit has drilled through and exited the second cortical layer of the bone; and in response to determining that the drill bit has drilled through and exited the second cortical layer of the bone, stopping the driving of the drill bit. In some embodiments, the step of determining whether the drill bit has drilled in the first cortical layer of the bone comprises comparing a difference between a first pair of consecutive torque values to a first threshold. In some embodiments, the method further comprises determining at least one of: whether the drill bit has drilled through an entry point of the second cortical layer of the bone; and whether the drill bit is drilling in the second cortical layer of the bone.

In some embodiments, in response to a determination that the drill bit has drilled through the entry point of the second cortical layer of the bone or a determination that the drill bit is drilling in the second cortical layer of the bone, the method further comprises determining an average torque value, the average torque value representative of torque values measured when the drill bit is drilling in the second cortical layer of the bone. In some embodiments, the method further comprises determining a difference between a first torque value and the average torque value, the first torque value being a current torque value measured by the torque-limiting surgical driver. In some embodiments, the method further comprises limiting the amount of torque applied to the drill bit in response to a determination that the first torque value is less than the average torque value.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

The preceding summary is meant to be a high-level summary of certain features within the scope of this disclosure. The summary, the following detailed description, and the associated drawings do not limit or define the scope of protection. The scope of protection is defined by the claims. No feature is critical or indispensable.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

DETAILED DESCRIPTION OF CERTAIN EMBODIMENTS

Various features and advantages of the disclosed technology will become more fully apparent from the following description of the several specific embodiments illustrated in the figures. These embodiments are intended to illustrate the principles of this disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein.

Overview of the Surgical Driver

Various embodiments of torque-limiting devices, systems, and methods are disclosed. For purposes of presentation, the devices are called "surgical drivers." A surgical driver can be any powered device capable of drilling a drill bit into, for example, a bone of a patient. Several embodiments are configured to drive drill bits into a bone. However, the features, characteristics, and/or operation of the surgical drivers described herein can be applicable in other contexts. For example, the features, characteristics, and/or operation of the surgical drivers described herein can be applicable to drive screws into a bone. Additionally, while the phrase "surgical driver" is used herein, such phrase does not limit this disclosure only to "surgical" contexts. Rather, the devices, methods, systems, features, characteristics, and/or operations discussed herein can be applicable to other contexts as well.

As more fully described below, the devices, systems, and methods can determine when to stop a drill bit being driven into various types and/or layers of bone so as to avoid "plunging" through the bone and potentially damaging nearby tissue. The term "plunging" refers to when a drill bit transitions from a state where it is drilling through bone to a state where it breaches the bone and advances away from the bone and into and/or through nearby tissue proximate to the bone.

Certain embodiments of the disclosed surgical drivers can be used, for example, as a powered surgical device in an on-plane form factor, a powered surgical device in an on-plane form factor for clavicle applications, a powered surgical device in an on-plane form factor for spinal applications, a powered surgical device in an on-plane form factor for extremities, and/or a powered surgical device in an on-plane form factor for large bone. The surgical drivers can be used for other procedures as well, and the particular procedure is not limiting. In some embodiments, the surgical driver can be operated remotely, for example, through the use of robotics.

Figure 1:
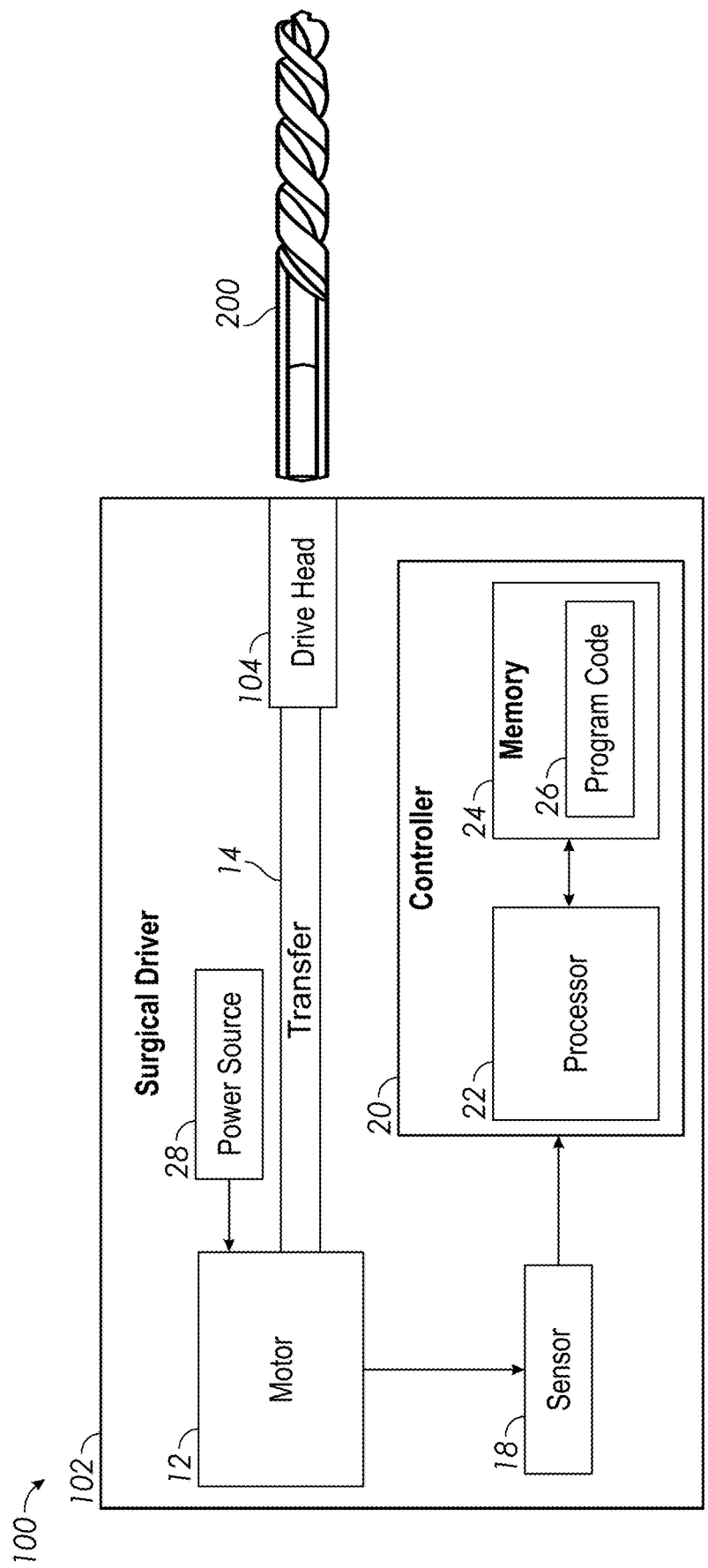
FIG. 1 schematically illustrates an example embodiment of a surgical driver.

As shown in FIG. 1, a torque-limiting surgical driver 100 can include a body 102 (also called a "housing," "handle," or "casing") that supports a motor 12. A transfer assembly 14 (e.g., one or more shafts, gears, etc.) operably connects the motor 12 to a drive head 104 at a distal end of the surgical driver 100 such that the motor 12 can turn the drive head 104. The drive head 104 can receive a drill bit 200 (also referred to herein as "bit") capable of drilling through portions of bone of a patient. Thus, the drill bit 200 can be positioned at a desired location on a substrate (e.g., a bone) and the motor 12 can be operated to drive the drill bit 200 into the substrate. In some applications, the motor 12 can be operated to rotate the drive head 104 to drive the drill bit 200 into and/or through portions of a bone, such as a clavicle bone. In some embodiments, the head 104 can receive a bit that engages with and drives a surgical screw of other fastener.

In some variants, the motor 12 is powered by a power source, such as a source of AC or DC electrical power. In some embodiments, the motor 12 is powered by an on-board power source 28, such as a battery, capacitor, or otherwise. In some embodiments, the motor 12 is configured to receive power from an external source, such as from a console, wall socket, or other external power source. In some embodiments, the motor 12 is a brushless DC motor. In some embodiments, the motor 12 is a three-phase electric motor. The motor 12 can include one or more hall sensors, which can send signals to the controller 20 to enable the controller 20 to determine the number of revolutions of the motor 12. In certain variants, the controller 20 determines the number of revolutions of the bit 200 from the number of revolutions of the motor 12.

The surgical driver 100 can monitor and/or limit the torque that the surgical driver 100 is applying to the drill bit 200 during the drilling process. For example, as described in more detail below, the surgical driver 100 can include a sensor 18 that senses the current supplied to the motor 12. The sensor 18 can send such data to a controller 20, which can include a processor 22 coupled with a memory 24, along with other electronic components. Because, in some implementations, the current supplied to the motor 12 can be proportional to the torque applied to the drill bit 200, the controller 20 can dynamically determine the amount of torque being applied to the drill bit 200. In certain variants, the controller 20 is configured to determine or receive signals indicative of one or more of the following data features: current supplied to the motor 12, number of revolutions of the drill bit 200 and/or motor 12, speed of the motor 12, or otherwise.

As described in more detail below, various embodiments of the surgical driver 100 can include one or more algorithms adapted to limit and/or control the torque applied to a drill bit 200. The algorithms can be included in the memory 24 as program code 26 to be implemented on a computer-readable non-transitory medium. The processor 22 can execute the program code 26 to perform various operations, such as determining a torque limit, instructing the motor 12 to cease operation, instructing a power source 28 to reduce and/or stop providing power to the motor 12, or other operations. The processor 22 and/or program code 26 can control and/or implement any of the features described in this disclosure, such as any of the torque-limiting features. Some implementations are configured to stop the rotation of the drill bit 200 by shutting-off (e.g., substantially or totally) the power to the motor 12. Certain implementations include a brake to actively decelerate the motor 12 or components. For example, some implementations include a friction or electromagnetic brake.

In various embodiments, the surgical driver 100 can include one or more computers or computing devices that implement the various functions described herein under the control of program modules stored on one or more non-transitory computer storage devices (e.g., hard disk drives, solid state memory devices, etc.). Each such computer or computing device typically includes a hardware processor and a memory. Where the surgical driver 100 includes multiple computing devices, these devices may, but need not, be co-located. In some cases the surgical driver 100 may be controlled by cloud-based or shared computing resources, which can be allocated dynamically. The processes and algorithms described herein may be implemented partially or wholly in application-specific circuitry, such as Application Specific Integrated Circuits and Programmable Gate Array devices. The results of the disclosed processes and process steps may be stored, persistently or otherwise, in any type of non-transitory computer storage such as, e.g., volatile or non-volatile storage.

Figure 2A:
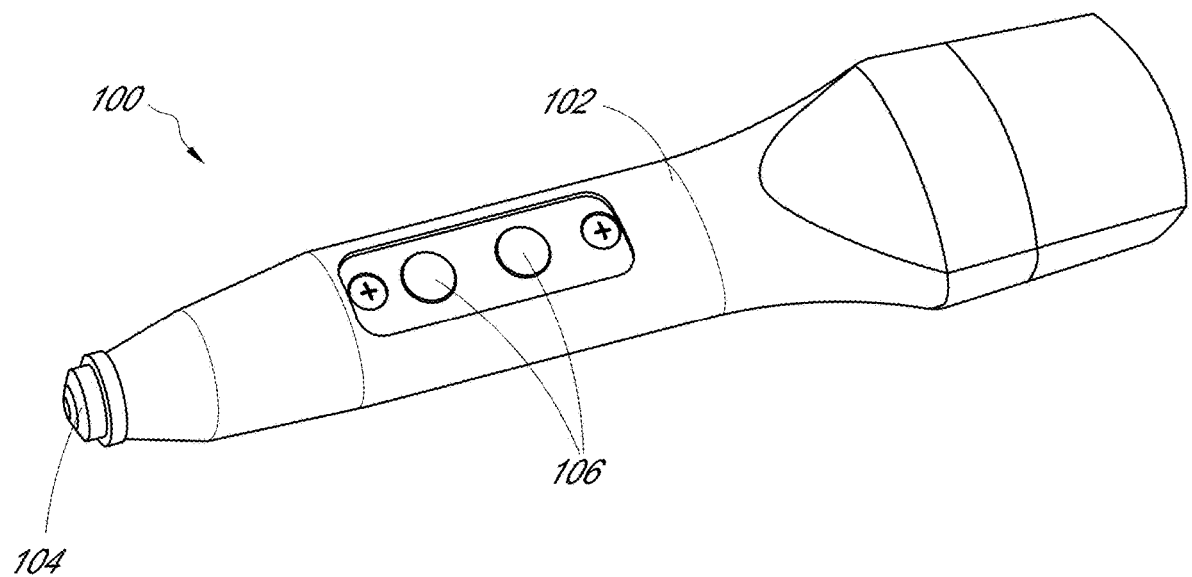
FIG. 2A illustrates a perspective view of the surgical driver of FIG. 1.

FIG. 2A further illustrates an example of a surgical driver 100. As shown, the body 102 of the surgical driver 100 can include an input device 106, such as buttons, switches, or otherwise. Through the input device 106, a user can control aspects of the operation of the surgical driver 100, such as the controller 20. For example, the user can instruct the surgical driver 100 regarding rotational direction (e.g., forward or reverse), speed, and/or otherwise. The input device 106 may power the surgical driver 100 on or off, or maintain the surgical driver 100 in standby mode. In some embodiments, the surgical driver 100 may have variable speed options as well as forward and reverse capabilities.

Figure 2B:
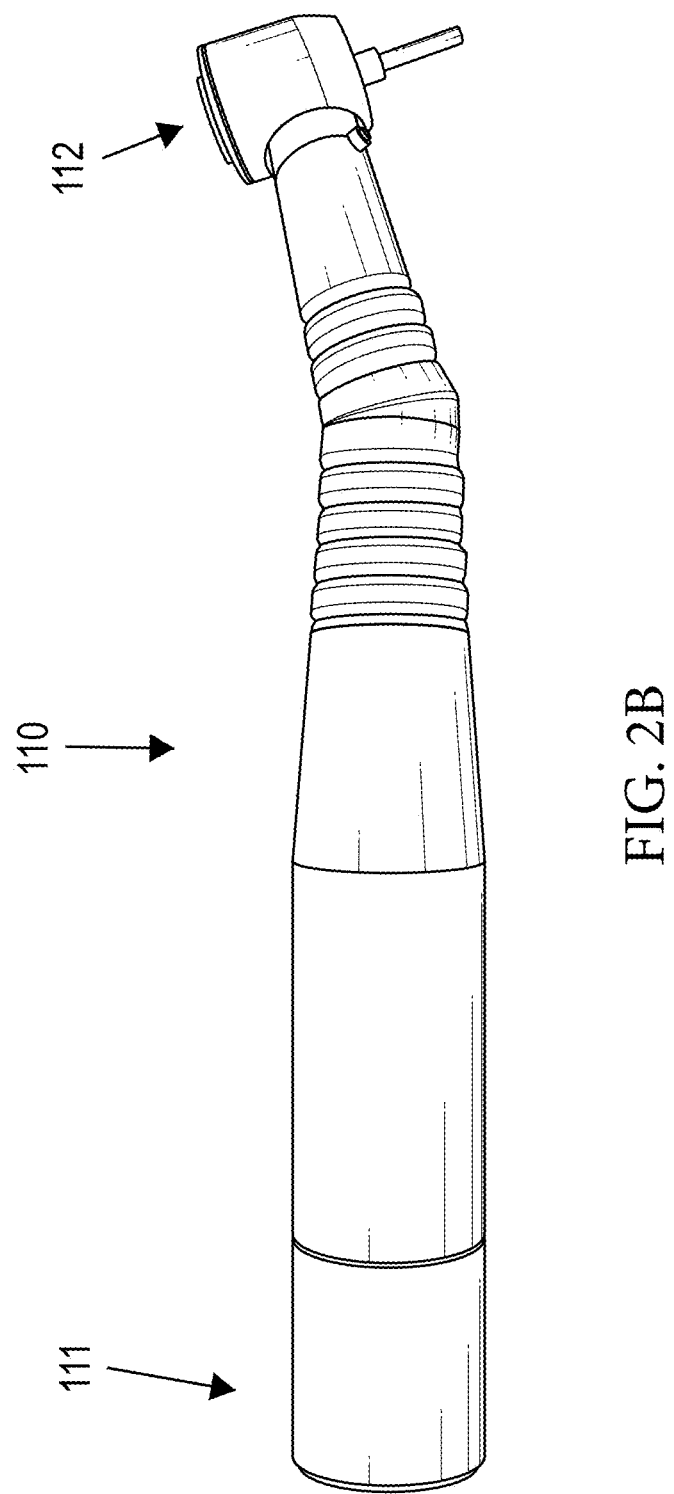
FIG. 2B illustrates an attachment that can be used with the surgical driver of FIG. 1.

In some embodiments, different attachments can be removably attached to the surgical driver 100, such as at a collet of the surgical driver 100. An example of an attachment 110 is shown in FIG. 2B. The attachment 110 can allow a user to access harder to reach areas, e.g., as shown, the attachment can include an offset of about: 40°, 50°, 60°, 70°, 80°, 90°, 100°, 110°, 120°, or other values. The attachment 110 can change the rotational plane of the surgical driver 100. Further, the attachment 110 may be an extension for further reaching positions. The attachment 110 can be selectively connected to and/or removed from the surgical driver 100, such as by connecting or disconnecting from a collet of the surgical driver 100. As illustrated, the attachment 110 can comprise a low-profile and/or elongate configuration and can extend the reach of activity. This can be beneficial in certain types of procedures, such as certain thoracic procedures involving a posterior approach to access anterior ribs. In some embodiments, the attachment 110 comprises an extension adaptor with a first end 111 and a second end 112. The first end 111 can be configured to mate with the drive head 104 of the surgical driver 100. The second end 112 can include a drill bit and/or can be configured to mate with a drill bit and/or can be configured to mate with a screw. The attachment 110 can include a power transmission assembly (e.g. a drive shaft) that operably connects the drive head 104 of the surgical driver 100 to the second end 112 of the attachment 110. For example, the power transmission assembly can convey rotational motion from the drive head 104 to the second end 112 of the attachment 110. In various embodiments, the attachment 110 is configured to enable drilling into a target site (e.g., a bone) that is spaced a substantial distance apart from the body 102 of the surgical driver 100 (e.g., at least about: 10 mm, 25 mm, 50 mm, 75 mm, 100 mm, 150 mm, 200 mm, 250 mm, 300 mm, distances between the aforementioned distances, or other distances). In some embodiments, the attachment 110 has a reflective and/or mirror-like surface, which can be added, attached, or integrated into the attachment 110 to enhance visibility of the target site. The attachment 110 can be articulating or fixed with respect to the body 102 of the surgical driver 100. The attachment 110 can be configured for use with the surgical driver 100, which can include torque-limiting functionality. In some embodiments, the attachment 110 is configured for use with a driver device that does not include torque-limiting functionality.

In some embodiments, the surgical driver 100 can include a mode switch (or similar mechanism) that can allow the user to toggle between modes, such as the powered and manual modes discussed below. In some embodiments, the mode switch can change the parameters of the surgical driver 100 based on a specific type of drill bit. In some embodiments, the mode switch can allow the surgical driver 100 to recognize the presence of different adapters or attachments.

In some embodiments, the body 102 may provide a user with visual output on certain parameters of the surgical driver 100, such as, power status, mode, speed, or otherwise. Some embodiments are configured to provide trajectory orientation, such as through the use of MIMS (Medical Information Management System), MEMS (Micro-Electromechanical Systems), gyroscopic, or other technology that can cue a user about the orientation of the surgical driver. In some embodiments, the surgical driver 100 is configured to indicate (e.g., to a user) deviations from a "zeroed" orientation, such as the angular deviation from a horizontal or vertical position. In some embodiments, the body 102 can include an LED or LCD display to provide information, to the user. In some embodiments, the surgical driver 100 can connect to an outside display, such as a monitor, such as through a wireless network, to provide a visual output to the outside display. In some embodiments, haptic cues (e.g., small vibrations) can provide information to the user. In some embodiments, electromagnetic field (EMF) or Hall Effect sensors can be incorporated into embodiments of the surgical driver 100.

Various shapes of the surgical driver 100 are contemplated. For example, some embodiments are on plane, which can enhance feel. In this disclosure, the term "on plane" describes a device with a generally linear arrangement. This is in contrast to "off plane" devices, which generally have an L-shaped arrangement, such as a pistol grip. In some embodiments, the surgical driver 100 has an on plane configuration in which the tip is generally in line with the user's hand, such as the tip and the handle being generally collinear. In some variants, the surgical driver 100 has an off plane configuration, such as having a pistol grip.

An on plane configuration can have a number of advantages. For example, an on plane configuration can allow a user to apply force through the surgical driver to the screw along a linear axis, rather than, for example, through a curve or elbow. In some implementations, an on plane design reduces or eliminates a moment of force that can be associated with certain pistol grip designs, such as due to force being applied to the handle of the pistol grip device and then being transferred through the barrel of the pistol grip device. Reducing or eliminating the moment can increase control of the screw and/or decrease user fatigue (e.g., by reducing exertion needed to counteract the moment). Some embodiments with an on plane configuration can avoid or reduce slippage of the drill bit 200 relative to the substrate, or at least increase the chance that such slippage will occur generally in a desired direction. For example, the on plane arrangement can locate the fingers closer to the drill bit than a pistol grip design, which can enable the user to better detect when slippage is occurring, or is about to occur, and to take action in response.

In some embodiments, an on plane configuration allows a user to use larger muscles (e.g., muscles of the upper arm) compared to pistol grip devices (e.g., which may require usage of wrist muscles or other smaller muscles). The engagement of the larger muscles can provide greater strength and/or control. In some embodiments, there may be no cantilever or no pistol grip.

The on plane arrangement can provide an improved weight distribution, such as by removing weight from a cantilever from the handle. In some arrangements, an on plane configuration can enhance the sensitivity with which a user can discern characteristics of the drill bit and/or the substrate. For example, while large muscles can control the initial driving, the fingers, located closer to the tip than if an off plane arrangement, can be used for final manipulations. Thus, the user can use their fingers for fine-tuning, which can provide more dexterity when handling the surgical driver. Further, the on plane arrangement can dampen vibrations as the surgical driver is being held by the larger arm muscles. Moreover, by stabilizing with the large arm muscles and using the wrists/fingers to manipulate, there can be less migration of the surgical driver, especially caused by unwanted jolts, as compared to an off plane arrangement, which uses a larger moment arm and thus is more susceptible to jerks/movements.

In some embodiments, the sleek form factor of the device can reduce packaging sizes, thus resulting in cost savings. Certain embodiments can ease the transition from manual surgical drivers to powered surgical drivers, can increase visibility of the tip and tissues into which the driving is occurring, and/or can reduce weight of the surgical driver which can mitigate user fatigue.

In some embodiments, the surgical driver 100 can be partially or fully cannulated and/or configured to be cannulated. This can allow the threading of a guidewire and/or k-wire (or other wire, the type of which is not limiting) through the surgical driver 100. Further, the cannulation can allow for suction to be used in conjunction with the surgical driver 100. The cannula can extend through the entirety of the surgical driver 100 (e.g., from back to front), or can include an aperture on a side of the body 102 that can lead to a tip (or near a tip) of the surgical driver 100. The cannula can general extend along (or be parallel with) a longitudinal axis of the surgical driver 100.

Further, in some embodiments, the motor 12 itself within the surgical driver 100 can be cannulated as well. Thus, a cannula can extend through at least a portion of the motor of the surgical driver 100. The motor 12 can be partially or fully cannulated and/or configured to be cannulated. The cannula can extend through the entirety of the motor 12 (e.g., from back to front), or can include an aperture on a side of the body 102 that can lead to a tip (or near a tip) of the surgical driver 100. In some embodiments, the cannula can generally extend along (or be parallel with) a longitudinal axis of the motor in the surgical driver 100. The cannulated motor can be used for a number of different applications including, for example, using a cannulated motor in a powered surgical device, using a cannulated motor in an on-plane powered surgical device, using a cannulated motor in an on-plane powered surgical device for clavicle applications, using a cannulated motor in an on-plane powered surgical device for spinal applications, using a cannulated motor in an on-plane powered surgical device for extremities, and/or using a cannulated motor in an on-plane powered surgical device for large bone applications. However, the cannulated motor can be used for other procedures as well, and the particular procedure is not limiting.

In some embodiments, the body 102 can include different shaped handles (or grips). The different handles can be used to replace a portion of the body 102, and thus can be integrally formed with the body 102 in some embodiments. In some embodiments, different handles can be detachable from a proximal end of the body 102, thus allowing a user to choose which particular handle suits the needs of a particular use (e.g., surgery). In some embodiments, the handles can be switched out during surgery by the surgeon. For example, the handles can have an attachment mechanism to the body 102, such as through male/female threading, snaps, fasteners, or other non-limiting removable attachment devices.

Figure 3:
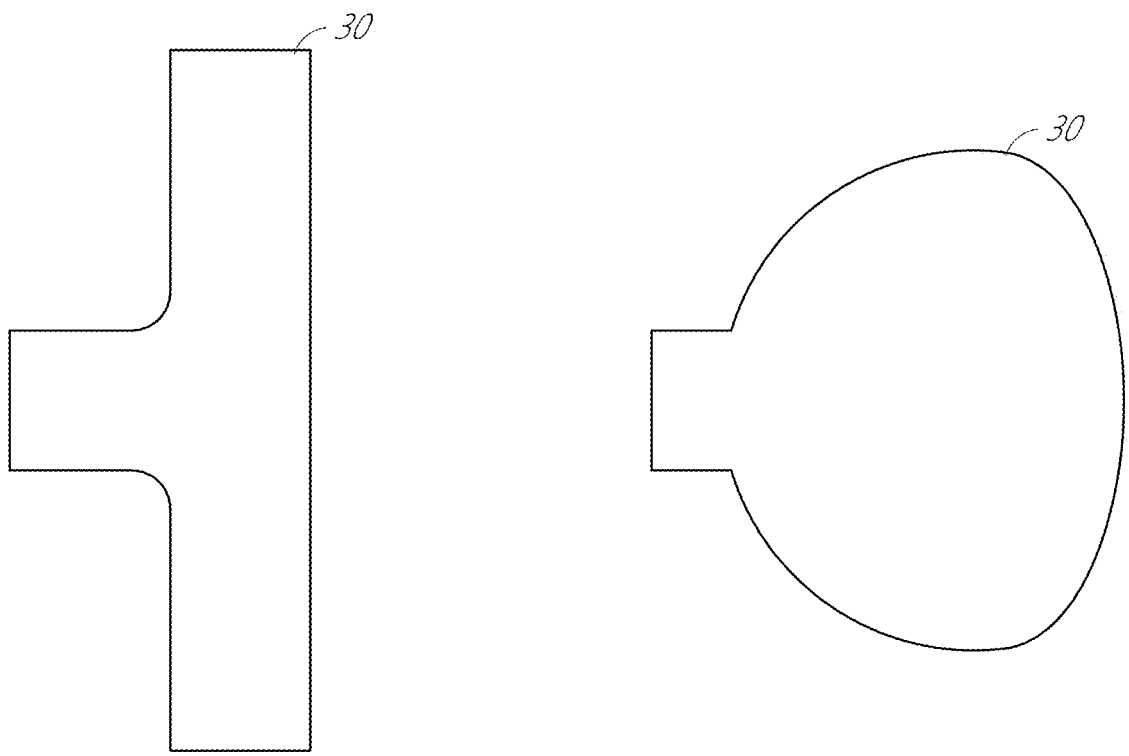
FIG. 3 illustrates example end views of handle shapes for embodiments of a surgical driver.
Figure 4:
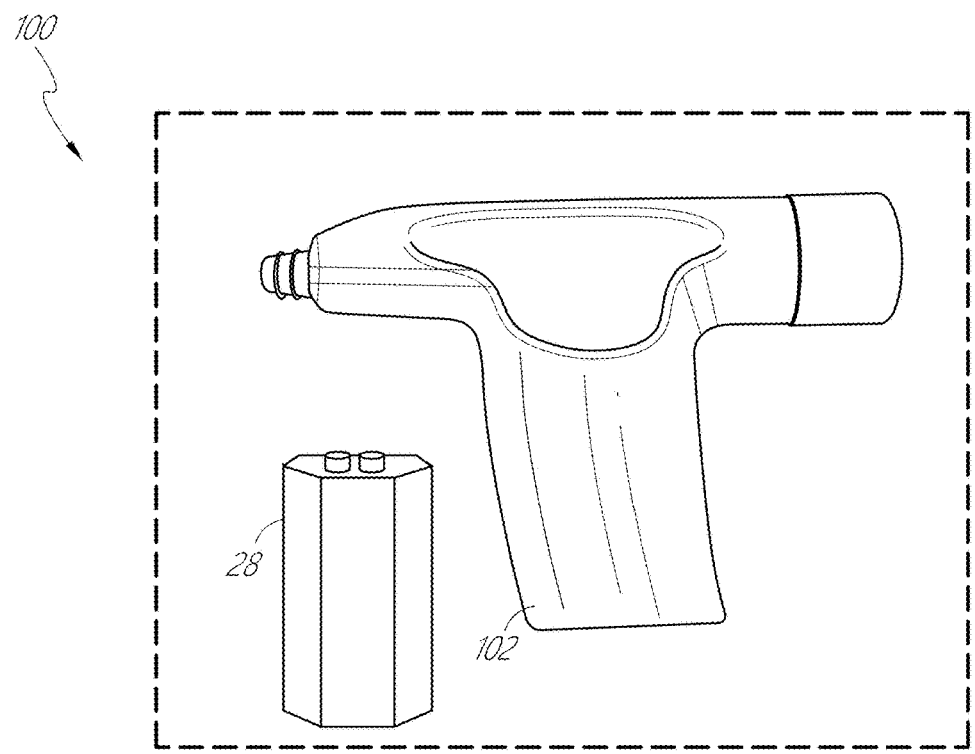
FIGS. 4-7 illustrate examples of a surgical driver comprising a body with a handle that includes a power source, such as a battery.

The handles can be made from a number of different materials, such as metal, plastic, or rubber, and can come in a variety of different shapes. Handles can further include gripping features such as bumps or divots that make it easier for a user to control the handle. FIG. 3 illustrates example cross-sectional shapes of handles 30 that can be used with the surgical driver as disclosed herein. As show, these handles 30 can have a generally "T" shape (FIG. 3 left) or generally circular or ball shape (FIG. 3 right). While these two particular handles 30 are illustrated, other handles can be used as well, such as generally "J" shaped, pistol grip, or closed ring handles, or otherwise. The particular handle shapes and dimensions of FIG. 3 are not limiting.

FIGS. 4-7 illustrate another example of the surgical driver 100. The surgical driver 100 has a body 102 with a handle that can be grasped by a user. In the embodiment illustrated, the handle has a pistol grip configuration. In some implementations, the surgical driver 100 is approximately 7 inches long. The surgical driver 100 can have a power source, such as a battery 28. The power source 28 can fit in the body 102, such as in the handle.

Figure 5:
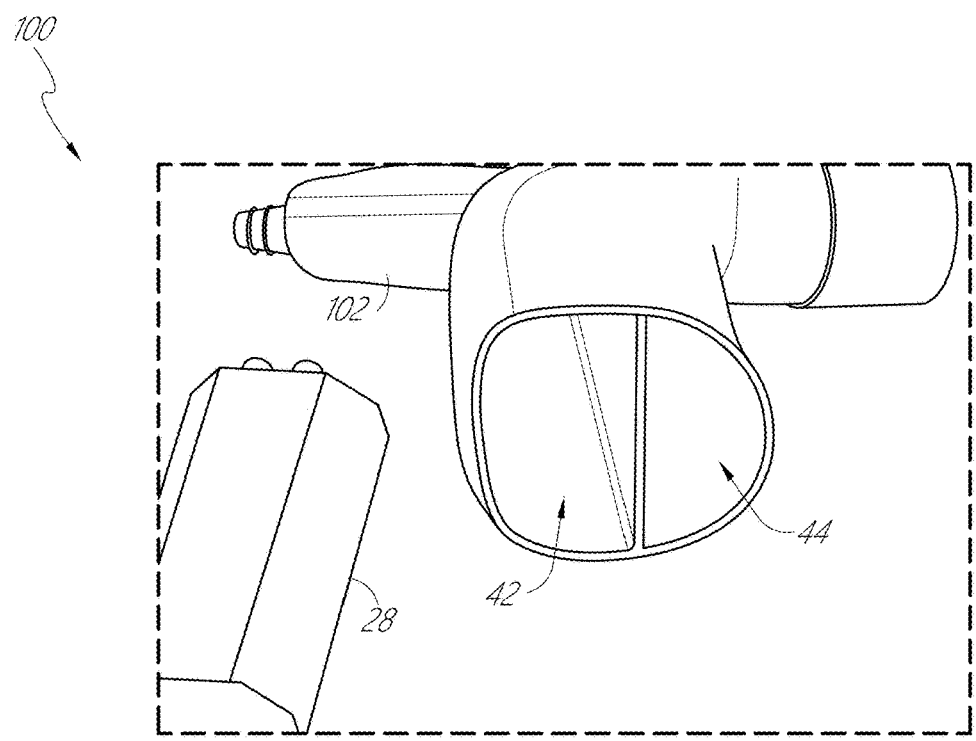

FIG. 5 shows the bottom opening of the body 102. The body 102 can have multiple cavities, such as a first cavity 42 that is designed to hold the battery 28 and a second cavity 44 that is designed to hold electronics, such as circuit boards. After the circuit boards are installed, a cover plate can be affixed to seal the second cavity 44 from moisture intrusion. Having the boards and battery both inserted into the handle allows the length and profile of the surgical driver 100 to be reduced.

Figure 6:
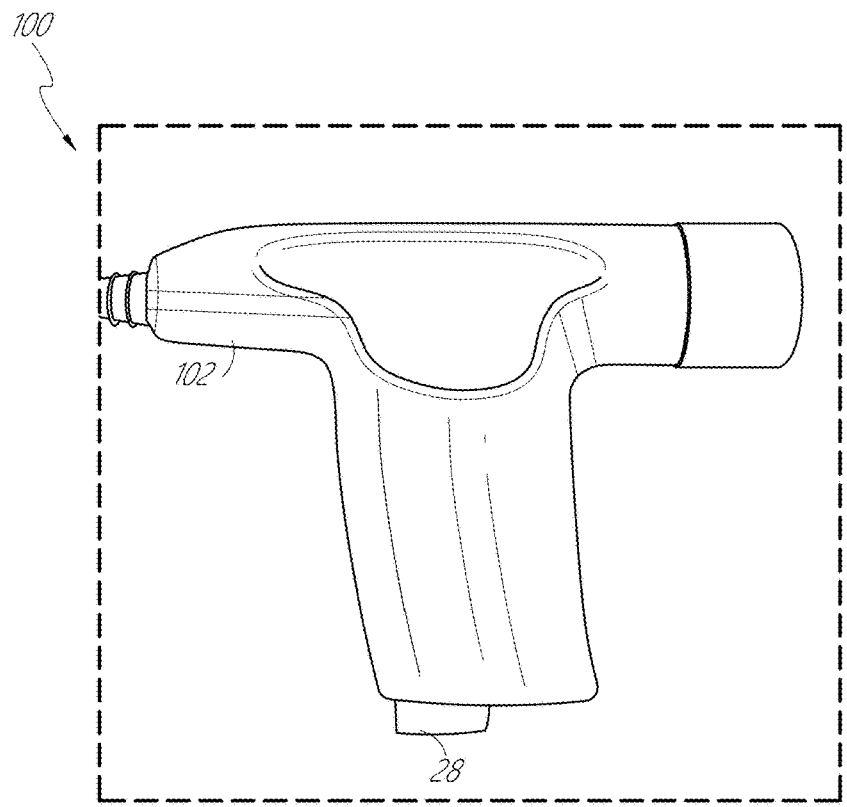
Figure 7:
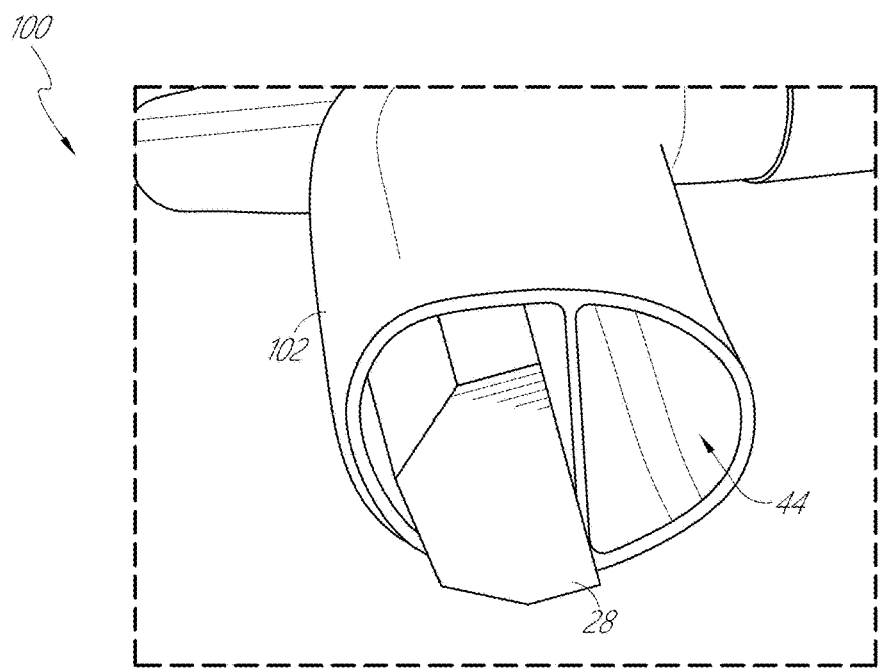

FIG. 6 shows the battery 28 placed in the handle of the body 102 of the surgical driver 100. In some implementations, the battery 28 is fully enclosed in the body 102. A fully enclosed battery 28 can ensure that the battery 28 is not exposed to bio-material during operation. In some embodiments, the battery 28 is contained and/or sealed with a door. FIG. 7 shows the battery 28 inside the handle. The surgical driver design could include a mechanism that covers the battery 28 from the bottom and forces it up into the handle. This feature will ensure that the battery 28 engages the power contacts with the surgical driver 100 during use. In some embodiments, this mechanism may be hinged on one side to function like a trap door. In other embodiments, this mechanism may be pinned at one corner to rotate over or away from the cavity to allow the battery 28 to be inserted.

Various embodiments of the surgical driver 100 have a variety of operational characteristics. For example, some embodiments provide a maximum rotational speed (at no load) of at least about: 3,000 rpm, 4,000 rpm, 5,000 rpm, 6,000 rpm, 10,000 rpm, values between the aforementioned values, or other values. Some embodiments can slow the rotation of the drill bit 200 after a slowdown point has been reached. Certain such embodiments have a slowed speed (at no load) of less than or equal to about: 500 rpm, 600 rpm, 700 rpm, 800 rpm, 900 rpm, 1,000 rpm, 1,100 rpm, 1,200 rpm, values between the aforementioned values, or other values. Certain implementations of the surgical driver 100 can provide a torque on the drill bit 200 of at least about: 25 in-oz, 30 in-oz, 35 in-oz, 40 in-oz, 45 in-oz, values between the aforementioned values, or other values. Some embodiments of the surgical driver 100 can provide a torque on the drill bit 200 of at least: 25 N-cm, 30 N-cm, 35 N-cm, 40 N-cm, 45 N-cm, values between the aforementioned values, or other values.

Various embodiments of the surgical driver 100 include a forward input that a user can engage to instruct the surgical driver 100 to turn the drill bit 200 in a forward direction, such as in the direction to drill the drill bit 200 into the bone. For example, the forward input can be a switch, button, dial, trigger, slider, touchpad, or the like. Certain embodiments have multiple input members, such as a fast forward switch (e.g., the motor will spin at about 4100 RPM at no-load) and a slow forward switch (e.g., motor will spin at 500 RPM at no-load). Some implementations have a reversing input, which can instruct the surgical driver 100 to turn the drill bit 200 in a reverse direction, such as in the direction to remove the drill bit 200 from the bone. The reversing input can be similar to the forward input, such as the options described above. In some embodiments, engaging the reversing input causes the motor to spin at about 500 RPM at no-load. In certain implementations, the final rotational speed of the drill bit 200 is about 500 RPM. In some embodiments, the forward input and the override input are the same component. In some implementations, the surgical driver 100 can includes an input device 106, such as buttons, switches, or otherwise, that can allow a user to select a mode of operation. For example, the user can choose between a mode in which the driver stops drilling before breach (e.g., before the drill bit exits out the opposite side of the bone) occurs and a mode in which driver stops drilling after breach occurs.

In various embodiments, the surgical driver 100 includes components configured to adjust the torque data, such as by filtering the torque data, decreasing noise in a signal from a sensor 18 (e.g., a motor current sensor), or otherwise. For example, the surgical driver 100 can include one or more low-pass filters. The filters can be implemented in hardware and/or software. For example, in some embodiments, the filters comprise resistance capacitor circuitry. Certain embodiments include a software filter configured to filter out certain frequencies and/or levels of torque data. In various embodiments, the filtering components can facilitate a smoother torque curve. In some variants, the filtering components can reduce errors in the torque-limiting functionality that may otherwise be caused by noise and/or outlier measurements. In some embodiments, conversion of current, voltage, power, etc. to torque values (such as nm, inch ounces, etc.) can be performed with a look up table or a mathematical equation.

In some embodiments, the surgical driver can incorporate additional features that can identify and/or differentiate the starting torque for an already seated screw from that of a screw that has just started, such as through a higher initial torque value, which can inhibit or prevent the device from continuing to drive and potentially strip an already seated screw. Further disclosure regarding torque-limiting surgical devices (such as regarding dynamically determining and/or limiting torque when attempting to secure a plate against a bone with a screw in order to inhibit or prevent the screw from stripping or damaging the bone of a patient) can be found in U.S. Pat. No. 10,383,674 filed on Jun. 6, 2017, which is hereby incorporated by reference in its entirety. Any of the features described in the '674 patent can be incorporated in the systems, devices, and methods disclosed herein.

Substrate Identification and/or Differentiation Overview

In some embodiments, data inputs (e.g., measurements performed during a portion or throughout a drill bit drilling procedure) can be used by a surgical driver 100 to make certain determinations. For example, the surgical driver 100 can be configured to use the data inputs to distinguish between and/or identify different types of tissues that the drill is being driven into. This can be called "tissue differentiation."

The data inputs can come from, for example, motor current and/or speed, though other methods of torque measurement can be used as well. In some embodiments, the data inputs comprise a measured torque, which can be data that is derived from or indicative of the torque being supplied by the surgical driver 100. In some implementations, the data inputs comprise current and/or voltage measurements, and one or more algorithms or data tables can be used to convert the inputs into torque values.

As discussed in more detail below, in some embodiments, the surgical driver 100 can use the data inputs, and/or changes in the data inputs, to determine a particular tissue type that the surgical driver 100 is driving the drill bit 200 into. For example, the surgical driver 100 can be configured to discern whether the drill bit 200 is being driven into soft tissue or bone based on the data inputs and/or changes in the data inputs. Further, the surgical driver 100 can be configured to discern between different soft tissues or different bone types or portions of bone (e.g., cortical and cancellous) based on the data inputs and/or changes in the data inputs.

In some embodiments, the data inputs and/or the determinations can be used to adjust operation of the surgical driver 100. For example, an algorithm (e.g., a discrete torque analysis algorithm) can use the data inputs to manage the drill bit velocity of the surgical driver 100. The algorithm can be used to adjust other characteristics/functionalities of the surgical driver 100, such as voltage, current, rotational speed of the drill bit, and/or power supplied to the motor. In some embodiments, the measured torque and/or changes in the measured torque can be used to control driving of the drill bit 200, such as stopping operation of the motor, changing the driving velocity of the drill bit 200, or other changes.

In some embodiments, the changes in torque can be presented (e.g., shown or displayed) to a user. For example, embodiments of the surgical driver 100 can include one or more indicators, such as lights or sounds, which indicate the drill bit 200 is being driven in a particular torque range and/or that the drill bit 200 is being driven in a particular tissue layer or type. For example, a first indicator can activate when the drill bit 200 is being driven into a first tissue type and/or layer, and a second indicator can activate when the drill bit 200 is being driven into a second tissue type and/or layer. The surgical driver 100 can include a display (e.g., an electronic screen) that displays certain information, such as the torque being applied to the drill bit, the type of tissue the drill bit is being driven into, or otherwise. The display can be located directly on the surgical driver 100, or can be through another connected visual device, such as a TV screen or monitor in which the surgical driver 100 is connected to, for example wirelessly or wired.

As discussed in detail below, the torque and/or changes in torque can be measured in a number of different ways. For example, torque measurements can be taken during some or all (and consistently or inconsistently) of the drill bit drilling procedure. In some implementations, variations between consecutive measurements can be provided to the user. In some embodiments, an alert is provided to the user when the measured torque is outside of a certain range or beyond a threshold. This threshold may be created, for example, by a user inputting a particular torque profile into the surgical driver 100 for a particular procedure. For example, the torque profile could be for the drilling of a drill bit 200 into a clavicle bone and could include pre-programmed thresholds for that particular procedure. Further, changes in the torque or other aspects of the torque, such as the first or second derivatives of torque measurements, may be provided to the user.

The surgical driver 100 can use tissue differentiation in a variety of applications and environments. For example, the surgical driver 100 can be configured to distinguish and/or identify different tissue types during a clavicle orthopedic surgery. However, other types of surgeries or procedures are possible.

Further disclosure regarding certain features related to torque-limiting surgical drivers can be found in U.S. Pat. No. 9,265,551, filed on Jul. 16, 2014 and U.S. Pat. No. 10,383,674, filed on Jun. 6, 2017, which are hereby incorporated by reference in their entireties. Any of the features (for example, certain torque-limiting features) disclosed in the '551 Patent and/or the '674 Patent can be used in conjunction with the surgical drivers disclosed herein.

The torque used to drill a drill bit through a given bone can vary significantly. One factor that affects the amount of torque required to drill the drill bit through a bone is the density of the bone, which can change based on the patient's age, gender, disease, and other factors. Typically, the denser the bone, the greater the force required to drill the drill bit. Additionally, density can change depending on the location of bone within the body.

Several torque-limiting methods, algorithms, and components are described below. Any method, algorithm, or component disclosed anywhere in this specification can be used in conjunction with any other method, algorithm, or component disclosed anywhere in this specification, or can be used separately.

"Anti-Plunge" Torque-Limiting Applications

As discussed above, in certain surgical procedures, medical professionals (for example, surgeons) utilize hand-powered instruments to drill into a bone of a patient. However, after drilling through an entry side of the bone (e.g., a first cortical portion of a bone), it can be difficult to determine when to stop the motor so as to inhibit or prevent "plunging" of the drill bit into tissue proximate an exit side of the bone, which can cause significant damage to the tissue. Embodiments of the surgical driver described herein can be configured to limit or stop operation of the motor and/or rotation of the drill bit when the surgical driver detects that the drill bit has breached or is close to breaching a bone. For example, embodiments of the surgical driver described herein can limit or stop operation of the motor and/or rotation of the drill bit: (1) when the surgical drill detects that the drill bit is drilling at or through a location close to an exit point or region of the bone; and/or (2) when the surgical drill detects that the drill bit breaches (exits), or has breached, the bone. With respect to "(1)" (also referred to herein as a "pre-breach" stage), some embodiments of the surgical driver described herein can limit or stop operation of the motor and/or rotation of the drill bit: (a) when the surgical drill detects that the drill bit has transitioned from a softer portion of bone (e.g., cancellous portion) to a harder portion of bone (e.g., cortical); and/or (b) when the surgical drill detects that the drill bit is currently located (and/or drilling) within a second layer of a harder portion of bone (e.g., cortical) and is thus close to an exit side of the bone. With respect to "(2)" (also referred to herein as a "post-breach" stage), some embodiments of the surgical driver described herein can limit or stop operation of the motor and/or rotation of the drill bit when the surgical drill detects that the drill bit breaches (exits), or has breached, the bone.

Figure 8:
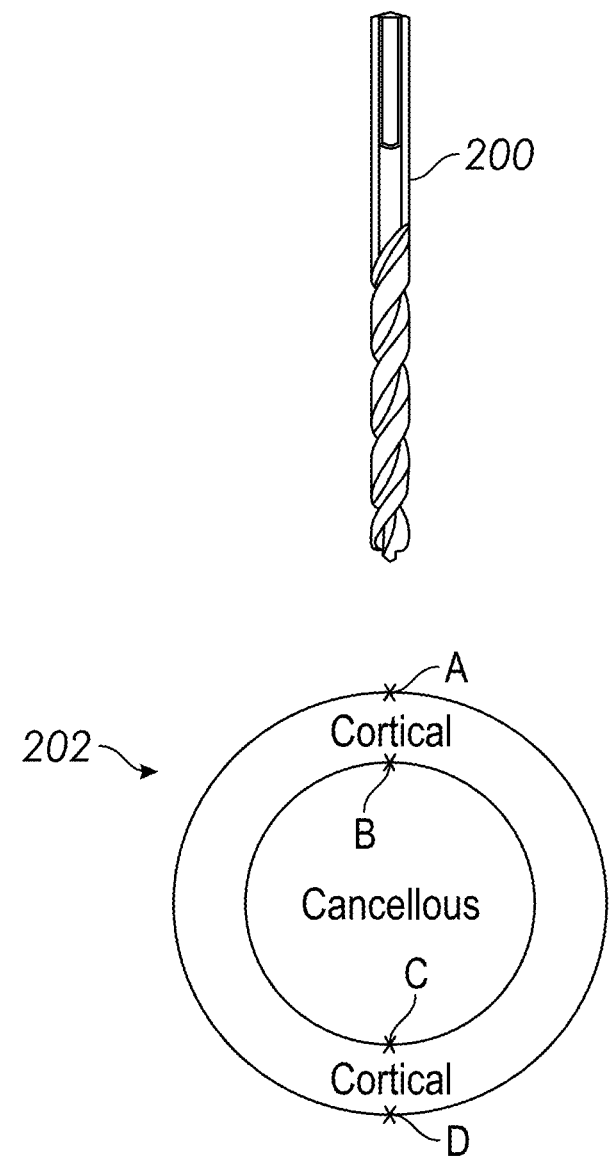
FIG. 8 schematically illustrates a drill bit and a cross-section of a bone in accordance with aspects of this disclosure.

FIG. 8 illustrates a simplified cross-section of a bone 202 of a patient. For example, bone 202 can be a clavicle, among others. Drill bit 200, which can be any type of drill bit capable of engaging and/or drilling through bone 202, is shown proximate, but spaced away from bone 202. Drill bit 200 can be received and/or driven by drive head 104 and/or motor 12 as discussed previously with respect to surgical driver 100. In some surgical scenarios, a medical professional may desire to drill out and/or through bone 202 in order to clear material for a screw and/or plate to be utilized to repair the bone 202 or a portion thereof. As discussed above, the typical approach is to operate a surgical driver 100 so as to drill through a first side of the bone 202 with drill bit 200 (for example, at point A of bone 202) and stop immediately when the drill bit 200 breaches through a second, opposite side of the bone 202 (for example, at point D). However, it is difficult for medical professionals to know where the drill bit 200 is within the bone and/or when to stop the motor of the surgical driver. As discussed above, the ability to detect when the drill bit 200 has breached or is close to breaching the bone 202 is important to inhibit or prevent damage to nearby tissue proximate bone 202.

Surgical driver 100 can utilize various methods and/or algorithms to detect the location of the drill bit 200 within bone 202 and stop rotation of the drill bit 200 prior to breaching bone 202 and/or plunging into or through tissue proximate the breaching point of bone 202. Surgical driver 100 can measure torque values at various sequential times in order to monitor and/or detect the position of drill bit 200 within bone 202. For example, in certain embodiments, a measured amount of torque (or current drawn by the motor, or other methods of determining rotation/torque discussed herein) is sampled at a sampling rate, such as about every: 2 milliseconds (ms), 5 ms, 10 ms, 20 ms, 30 ms, or any value therebetween, or any range bounded by any combination of these values, although other values outside these ranges are possible. The torque and time data can be stored in memory 24 of the surgical driver 100. This can facilitate monitoring the change in the torque relative to time (e.g., a first derivative of the torque) and/or monitoring torque at discrete intervals defined by the sampling time (for example, every 10 ms). As noted above, the torque can be directly proportional to the motor power required to drill the drill bit 200. In several embodiments, the torque at a given time is determined by the controller 20, which receives a signal from the sensor 18 indicative of the current drawn by the motor 12.

Overview of Exemplary Torque-Limiting Procedures

Figure 9:
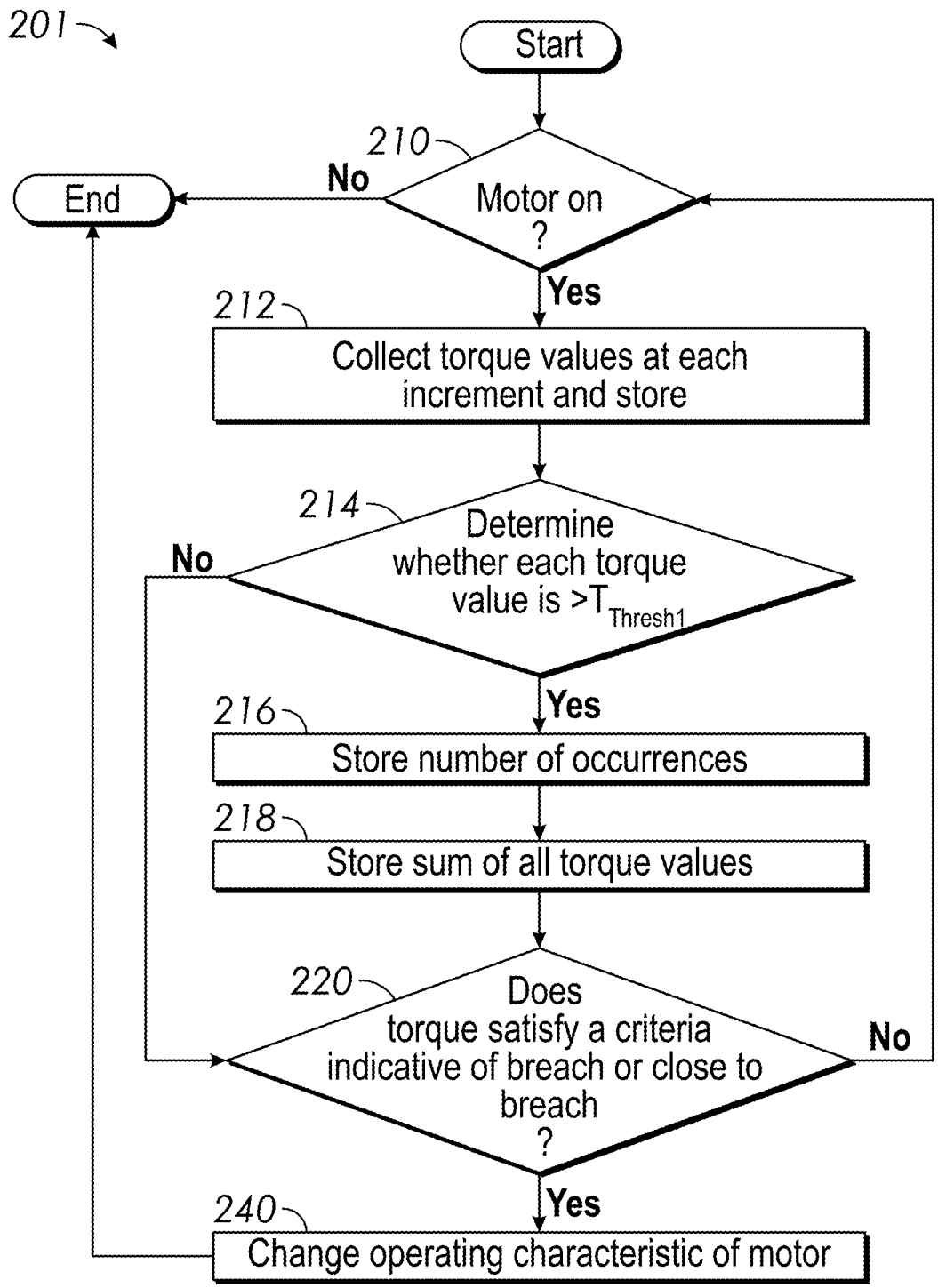
FIG. 9 illustrates an example method for torque-limiting drilling in accordance with aspects of this disclosure.

FIG. 9 illustrates an exemplary method and/or algorithm 201 of torque-limiting drilling in order to inhibit or prevent plunging of drill bit 200 through bone 202 and resulting damage to nearby tissue. FIGS. 10-13 illustrate further variations and/or details of exemplary method and/or algorithm 201.

The method 201 can begin after the driver 100 is on (e.g., energized). At block 210, the surgical driver 100 determines whether the motor 12 is on. Motor 12 can be turned on in response to a user activating an input (e.g., a button or switch) and the controller 20 instructing that power be supplied to the motor 12. The power can be used to begin turning the drill bit 200 received within and/or secured to the drive head 104. As shown in FIG. 9, if block 210 determines that motor 12 is not on, the method 201 can end. As shown in block 212, if it is determined that the motor 12 is on, the surgical driver 100 can begin collecting and/or storing torque values at a sampling rate, such as at 10 ms intervals as discussed above. The surgical driver 100 can collect the torque values via sensor 18, such as a sensor that can measure the amount of current being drawn by the motor 12. This current draw data can be used to determine the amount of torque because the current drawn by the motor 12 is generally proportional to the amount of torque that the motor is applying to drill bit 200 driven by the driver 100 (e.g., via drive head 104). The measured/collected torque values can be stored in memory 24 of driver 100.

As shown in block 214, the surgical driver 100 can (e.g., via controller 20 and/or processor 22) compare each collected and/or stored torque value to a first threshold $T_{Thresh1}$. This can be used to determine whether the drill bit 200 is engaging and/or drilling through bone 202, as opposed to merely rotating in air (e.g., free-spinning). The torque values detected when drill bit 200 is free-spinning through air are generally significantly lower than torque values detected when drill bit 200 is engaging and/or drilling through bone 202. In some implementations, the first threshold $T_{Thresh1}$ can be 0.035 in-oz, 0.036 in-oz, 0.037 in-oz, 0.038 in-oz, or 0.039 in-oz, or any range bounded by any combination of these values, or any value within a range bounded by any of these values, although other values are possible. As shown in block 216, if a given torque value is greater than or equal to the first threshold $T_{Thresh1}$, the controller 20 can collect/store each of such occurrence as a "count," the benefits of which are described further below. In some cases, the number of occurrences/times that measured torque values are greater than or equal to the first threshold $T_{Thresh1}$ can provide an indication of the thickness of the bone 202.

In some embodiments, the controller 20 tracks the torque data that meets certain requirements. For example, in the embodiment illustrated in FIG. 9, at block 218, the controller 20 can determine and store a sum of the torques that are greater than or equal to the first threshold $T_{Thresh1}$.

In various implementations, the controller 20 can use the torque data to deduce a location of the drill bit 200. For example, at block 220, the controller 20 can run a drill bit location analysis to determine the location of the drill bit 200 with respect to bone 202, as will be described further below. In some implementations, the controller 20 can run the drill bit location analysis regardless of whether a given torque value is greater than or equal to first threshold $T_{Thresh1}$ at block 214. Thus, blocks 214, 216, and/or 218 are not requirements for the operation of block 220. As discussed in more detail below, after the drill bit location analysis is conducted at block 220, the surgical driver 100 can be configured to determine whether to change an operating characteristic of motor 12. For example, the surgical driver 100 can be configured to determine whether to reduce or stop rotation of the drill bit 200 (via motor 12 and/or drive head 104) in response to a determination resulting from the analysis conducted at block 220 and to implement such a change. Such drill bit location analysis can include determining whether measured torque value(s) satisfy a criteria that indicates that the drill bit 200 has breach a bone or that is indicative that the drill bit 200 is close to breaching the bone. As shown in FIG. 9, if measured torque value(s) do not satisfy a criteria indicating that the drill bit 200 has breached or is close to breaching a bone, the method can return to block 210 and collect additional torque values.

Drill Bit Location/Torque Criteria Analysis

Figure 10:
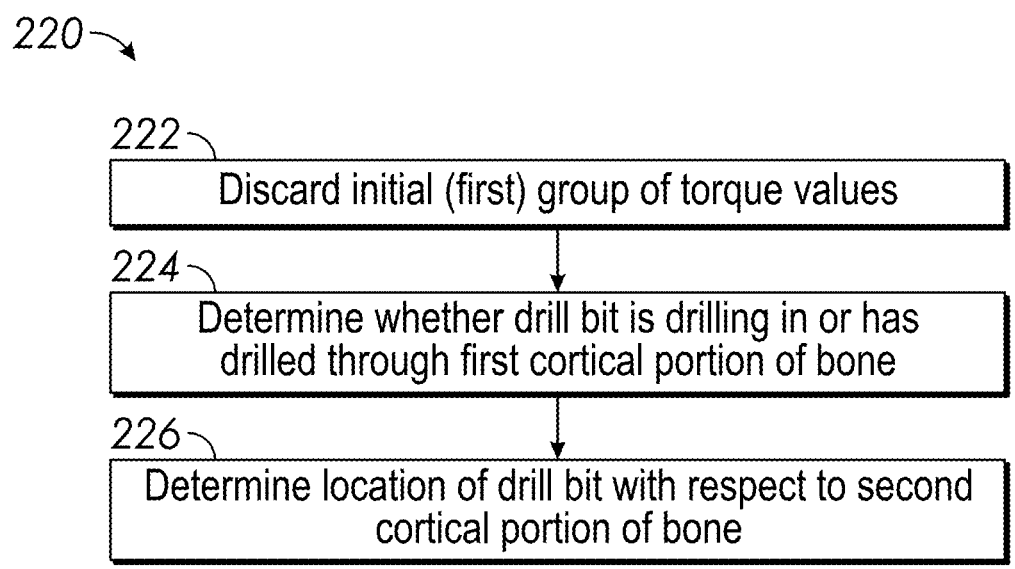
FIG. 10 illustrates a method of conducting a drill bit location analysis with can be used in the method of FIG. 9.

FIG. 10 illustrates block 220 in more detail. As discussed above, torque values can be collected at various sampling rates, for example, at every 10 ms. Before torque values over a given time period are used to determine the location of drill bit 200 within bone 202, it can be beneficial to ignore or discard a certain amount of initial values. For example, when motor 12 of surgical driver 100 is first turned on, there is a fair amount of "noise" originating from gears of the motor 12 which may produce variable torque values that do not represent engagement of the drill bit 200 with bone 202. Thus, at block 222, the controller 20 discards a first set or group of torque values before proceeding further with analysis. The amount of initial torque values that the controller 20 ignores or deletes can be equal to one, two, three, or four initial torque values, although other values are possible.

After block 222 is completed, controller 20 carries out blocks 224 and 226, each of which will be described in more detail below. At a high level, blocks 224 and 226 can determine the location of drill bit 200 within bone 202. More specifically, block 224 can determine whether the drill bit 200 is drilling, or has drilled, through or in the first cortical portion of bone 202. For example, with reference to FIG. 8, block 224 can determine whether the drill bit 200 is drilling, or has drilled, through or in the first cortical portion of bone 202 between points A and B of bone 202. Similarly, block 226 can determine the location of drill bit 200 with respect to the second cortical portion of bone 202 (for example, the portion of bone 202 between points C and D in FIG. 8).

As will be discussed in more detail below, determining the location of drill bit 200 with respect to the second cortical portion of bone 202 can involve determining, with the surgical driver 100 whether the drill bit 200 is in a "pre-breach" stage (e.g., close to breaching the bone) or whether the drill bit 200 is in a "post breach" stage (e.g., has breached the bone). Surgical driver 100 can determine that the drill bit 200 is in a pre-breach stage by determining whether the drill bit 200 is drilling at or through a location close to an exit point or region of the bone 202 (such as exit point D in FIG. 8). Surgical driver 100 can determine that the drill bit 200 is in a post-breach stage by determining whether the drill bit 200 is breaching (e.g., exiting), or has breached, an exit point or region of bone 202 (such as exit point D in FIG. 8). With respect to "pre-breach" and as further discussed below, in block 226 the surgical driver 100 can determine whether drill bit 200 has recently transitioned from the interior cancellous portion of the bone 202 to a second cortical portion of bone 202 and/or to determine whether drill bit 200 is currently drilling through this second cortical portion of bone 202. As discussed in more detail below, after the surgical driver 100 determines that the drill bit 200 is in a "pre-breach" or "post-breach" stage as the particular implementation is configured, the surgical driver 100 can change an operating characteristic of motor 12 in response at block 240. For example, the surgical driver 100 can shut off the motor 12 or decrease a rotation of the drill bit 200 in response to either of such determination(s).

Drill Bit Location with Respect to First Cortical Portion of Bone

Figure 11:
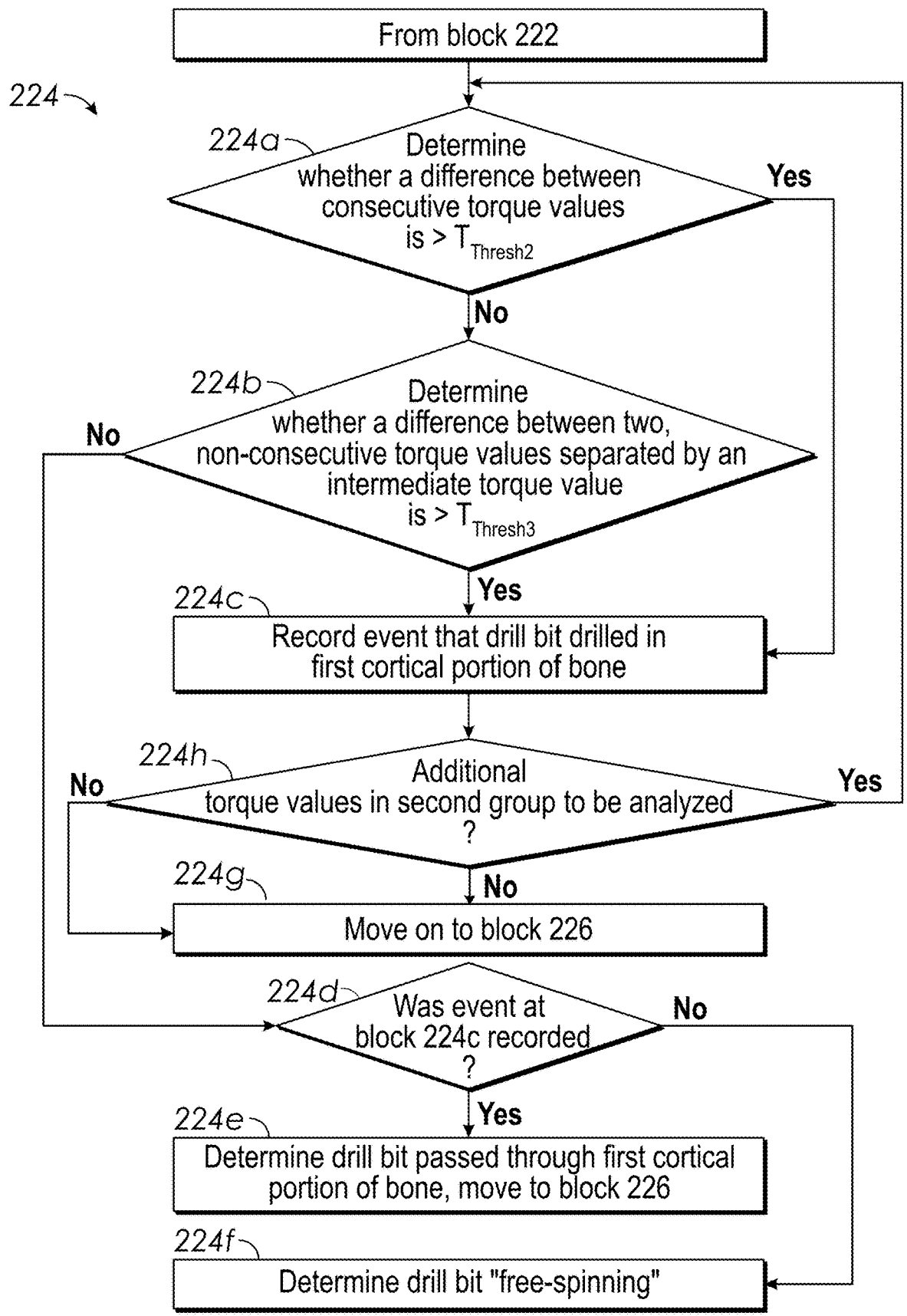
FIG. 11 illustrates a portion of the method of FIG. 10 in more detail.

FIG. 11 illustrates block 224 in more detail. As discussed above, a first group or set of torque samples collected (e.g., measured) by the surgical driver 100 can be ignored or discarded before further analysis is carried out according to block 220. This first group of samples can be the first three or four torque samples (e.g., torque values one through three or four), for example. As shown, at block 224a, a second group or set of torque samples can be collected and analyzed to determine whether the drill bit 200 is drilling, or has drilled, through or in the first cortical portion of bone 202. Such second group of torque samples can include a plurality of torque samples, such as five torque samples. For example, the second group of torque samples can be the fifth, sixth, seventh, eighth, and ninth torque samples and can follow the first group of discarded torque samples. Controller 20 can keep track of the maximum torque values experienced within the second group of torque samples, the benefits of which are described further with respect to block 226 below.

At block 224a, the second group of torque samples or a portion thereof (for example, torque samples 5-9) can be analyzed and/or compared to determine whether a difference between consecutive torque values within this second group is greater than or equal to a second threshold $T_{Thresh2}$. For example, controller 20 can determine whether a difference between a $7^{th}$ and a $6^{th}$ torque value (numbered consecutively with respect to the first group of torque values) within the second group is greater than or equal to the second threshold $T_{Thresh2}$ and/or whether a difference between a $6^{th}$ and a $5^{th}$ torque value (numbered consecutively with respect to the first group of torque values) within the second group is greater than or equal to the second threshold $T_{Thresh2}$. If one or both of such differences is greater than or equal to the second threshold $T_{Thresh2}$, then block 224a is affirmative. An affirmative block 224a can be indicative that the drill bit 200 is drilling through a hard portion of the bone 202, such as the first cortical portion of bone 202 at or between points A and B as shown in FIG. 8. If block 224a is affirmative, the surgical driver 100 can record and/or store the occurrence of such threshold exceedance as an event at block 224c (in memory 24). This can provide an indicator for the method that the first cortical portion of bone 202 has been encountered. As illustrated, the surgical driver 100 can analyze (e.g., compare) additional torque values within this second group, for example, until all the torque values within this second group have been analyzed according to blocks 224a-224g. For example, as shown in FIG. 11, if either of block 224a or block 224b are affirmative and lead to block 224c, the controller 20 can move to block 224h and determine whether there are additional torque values in the second group to be analyzed. If block 224h is affirmative, the controller 20 can return to block 224a and analyze remaining torque values according to blocks 224a-224c until block 224h is answered in the negative. Alternatively, in some embodiments, if block 224a is affirmative, the controller 20 of surgical driver 100 does not move to block 224h but instead moves from block 224c to block 226 (see block 224g), where additional analysis can be carried out as discussed further below. If block 224a is not affirmative, the method/algorithm can move to block 224b, where additional analysis can be carried out as described further below.

In some embodiments, the controller 20 can determine that the first cortical portion (e.g., between points A and B in FIG. 8) of bone 202 has actually been drilled through (e.g., through point B in FIG. 8). For example, in some variants, controller 20 is configured to detect that the drill bit 200 has passed through the first portion of cortical bone by detecting a decrease in the torque values. Certain embodiments are configured to determine that the first cortical portion of bone 202 has been bored through by: (1) recording an event at block 224c; (2) determining that blocks 224a and 224b return a "No" for subsequently collected torque values; and (3) analyzing both such results together (e.g., recognizing that "(1)" and "(2)" can indicate that an exit point of the first cortical portion has been drilled through).

The second threshold $T_{Thresh2}$ can be 0.00195 in-oz, 0.00196 in-oz, 0.00197 in-oz, 0.00198 in-oz, 0.00199 in-oz, 0.002 in-oz, 0.00201 in-oz, 0.00202 in-oz, 0.00203 in-oz, 0.00204 in-oz, or 0.00205 in-oz, or any range bounded by any combination of these values, or any value within a range bounded by any of these values, although other values are possible.

At block 224b, the second group of torque samples (e.g., torque samples 5-9) or a portion thereof can be analyzed and/or compared to determine whether a difference between non-consecutive torque values within this second group is greater than or equal to a third threshold $T_{Thresh3}$. For example, one or more non-consecutive torque samples within the second group that are separated by one intermediate torque sample can be compared to determine whether a difference therebetween is greater than or equal to the third threshold $T_{Thresh3}$. For example, controller 20 can determine whether a difference between a $9^{th}$ and a $7^{th}$ torque value is greater than or equal to the third threshold $T_{Thresh3}$ and/or whether a difference between a $7^{th}$ and a $5^{th}$ torque value is greater than or equal to the third threshold $T_{Thresh3}$. If one or both of such differences is greater than or equal to the third threshold $T_{Thresh3}$, this can be indicative that the drill bit 200 is drilling through the hard portion of the bone 202, such as the first cortical portion of bone 202 at or between points A and B as shown in FIG. 8. If one or both of such differences is greater than or equal to the third threshold $T_{Thresh3}$, the surgical driver 100 can record and/or store the occurrence of such threshold exceedance as an event at block 224c (in memory 24) which indicates that the first cortical portion of bone 202 is being drilled through. If one or both of such differences is greater than or equal to the third threshold $T_{Thresh3}$, at block 224h the surgical driver 100 can determine whether there are additional torque values within the second group to be analyzed. If block 224h is affirmative, the controller 20 can return to block 224a and analyze remaining torque values according to blocks 224a-224c until block 224h is answered in the negative. Alternatively, in some embodiments, if block 224b is affirmative and an event is recorded at 224c, the controller 20 of surgical driver 100 does not move to block 224h but instead moves from block 224c to block 226 (see block 224g), where additional analysis can be carried out as discussed further below.

If a difference between non-consecutive torque values (e.g., 2 values separated by one intermediate value) within this second group is not greater than or equal to the third threshold $T_{Thresh3}$, this can indicate either: (a) that the drill bit 200 has not engaged bone 202 (e.g., is free-spinning); or (b) that the drill bit 200 has already drilled through the first cortical portion of bone 202 (e.g., through point B of FIG. 8). To determine which of "(a)" or "(b)" is true, the controller 20 can check, at block 224d, whether an event at block 224c was previously recorded. If the controller 20 determines that event 224c was previously recorded, controller 20 determines, at block 224e, that the first cortical portion of bone 202 has already been drilled through (e.g., through point B in FIG. 8). In such cases, the drill bit 200 can be drilling through the softer, cancellous portion of bone 202. Alternatively, if the controller 20 determines that event 224c was not previously recorded and all of the second group of torque values have been collected (e.g., measured), the controller 20 determines, at block 224f, that the drill bit 200 is "free-spinning." In some embodiments, the controller 20 is configured to move to block 240 if it determines that the drill bit is free-spinning, which can stop or reduce rotation of the drill bit 200. This can advantageously conserve power (e.g., drawn from a power source) and/or processing power that would otherwise be utilized to further operate the motor 12 and carry out torque value analysis.

In some embodiments, the third threshold $T_{Thresh3}$ can be greater than the second threshold $T_{Thresh2}$. The third threshold $T_{Thresh3}$ can be 0.00215 in-oz, 0.00216 in-oz, 0.00217 in-oz, 0.00218 in-oz, 0.00219 in-oz, 0.0022 in-oz, 0.00221 in-oz, 0.00222 in-oz, 0.00223 in-oz, 0.00224 in-oz, or 0.00225 in-oz, or any value within a range bounded by any of these values, although other values are possible.

As discussed above, the controller 20 can move to block 226 after determining a "Yes" result from block 224a or 224b, or can wait to move to block 226 until all the torque values in the second group have been analyzed according to blocks 224a and 224b (e.g., via a determination at block 224h). As discussed above, at block 226, additional analysis can be carried out to determine where the tip of the drill bit 200 is with respect to the interior (e.g., cancellous) portion of bone 202 and/or the second cortical portion of bone 202 (e.g., at or between points C and D in FIG. 8). In some embodiments, if an event was recorded at block 224c (e.g., drill bit 200 was recorded as drilling through the first cortical portion of bone 202) and/or the controller 20 determined that the drill bit 200 has already drilled through the first cortical portion of bone 202 (block 224e), such determination can be advantageously used in further analysis when attempting to determine whether the drill bit 200 is currently in, or has recently drilled through the second cortical portion of bone 202 (e.g., at or between points C and D in FIG. 8), as discussed in more detail below.

Blocks 224a and 224b provide two methods by which drilling of the drill bit 200 through the first cortical portion of bone 202 can be detected. Comparing differences between one or more (or one or more sets of) consecutive torque values within the second group of torque samples (as done in block 224a) can be advantageous when drilling through thinner bone cross-sections (and, for example, thinner cortical portions of such bones). Comparing one or more (or one or more sets of) non-consecutive torque values separated by an intermediate torque value within the second group (as done in block 224b) can be advantageous when drilling through thicker bones or where a surgeon angles the drill bit 200 at an angle different than perpendicular to a surface of bone 202 (for example, at angles within 15 degrees from an axis perpendicular to such bone surface). Incorporating both blocks 224a and 224b advantageously allows controller 20 of surgical driver 100 to be used for both thin and thick bones and/or to predict whether the drill bit 200 is drilling through or in the first cortical portion of bone 202 (for example, between points A and B of bone 202 as shown in FIG. 8).

Drill Bit Location with Respect to Second Cortical Portion of Bone

As discussed above, the controller 20 can move to block 226 after block 224g or block 224e. As discussed above, at a high level, block 226 can aid in determining the location of drill bit 200 with respect to the second cortical portion of bone 202 (for example, the portion of bone 202 between points C and D in FIG. 8). As also discussed above, determining the location of drill bit 200 with respect to the second cortical portion of bone 202 can involve determining, with the surgical driver 100: (1) when the drill bit is drilling at or through a location close to an exit point or region of the bone 202 (such as exit point D in FIG. 8); and/or (2) when the drill bit breaches (exits), or has breached, an exit point or region of bone 202 (such as exit point D in FIG. 8). With respect to "(1)" and as further discussed below, in block 226 the surgical driver 100 can determine whether drill bit 200 has recently transitioned from the interior cancellous portion of the bone 202 to a second cortical portion of bone 202 (for example, has transitioned through an entry point C in FIG. 8) and/or to determine whether drill bit 200 is currently drilling through this second cortical portion of bone 202 (for example, is drilling through the second cortical portion and is located somewhere between point C and D in FIG. 8). Some embodiments of the surgical driver described herein can limit or stop operation of the motor and/or rotation of the drill bit when the surgical driver determines "(1)" (also referred to herein as a "pre-breach" stage). Some embodiments of the surgical driver described herein can limit or stop operation of the motor and/or rotation of the drill bit when the surgical driver determines "(2)" (also referred to herein as a "post-breach" stage).

As discussed above, the controller 20 of surgical driver 100 can collect torque values measured and/or communicated by sensor 18 at a sampling rate. As also discussed, a first group of torque samples can be discarded (see FIG. 10 and block 222) and a second group of torque samples can be utilized to determine whether drill bit 200 is drilling in and/or has drilled through the first cortical portion of bone 202 (see FIGS. 10-11 and block 224). Additionally, a third group of torque samples can be utilized to carry out the analysis of block 226. As a non-limiting example, the first group of samples can include four samples (for example, numbered samples 1-4), the second group of samples can include five samples (for example, numbered samples 5-9), and the third group of samples can include ten or more samples (for example, 16 samples numbers 10-25).

Figure 12:
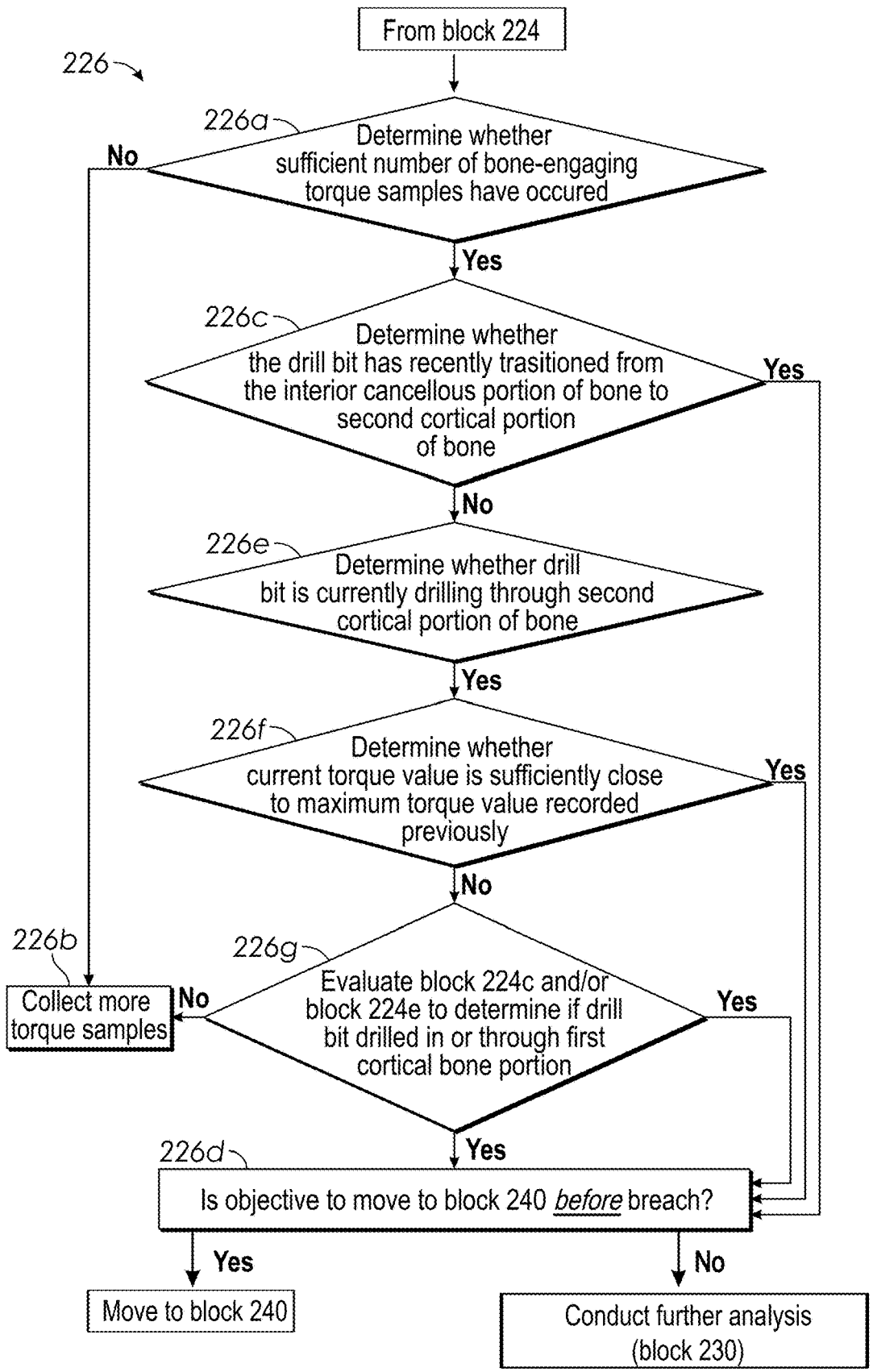
FIG. 12 illustrates a portion of the method of FIG. 10 in more detail.

In block 226, the third group of torque samples can be collected. The controller 20 can analyze (e.g., compare) one or more torque values within the third group of torque samples. This can aid in determining whether drill bit 200 has recently transitioned from the interior cancellous portion of the bone 202 to a second cortical portion of bone 202 and/or whether drill bit 200 is currently drilling through this second cortical portion of bone 202. Before carrying out such comparisons, as shown in FIG. 12, controller 20 can determine whether there have been a sufficient number of bone-drilling or bone-engaging torque samples at a given point in time (e.g., after a given amount of torque values have been sampled at a sampling rate). As discussed previously with reference to FIG. 9, controller 20 can track how many measured torque values are greater than or equal to the first threshold $T_{Thresh1}$, and where a given torque value is greater than or equal to such first threshold $T_{Thresh1}$, this indicates that that torque value represents a value experienced when the drill bit 200 is drilling into a material other than air (e.g., bone), which represents a "bone-engaging torque sample." At block 226a, if the number of bone-engaging torque samples is greater than or equal to a threshold percentage $P_{Thresh1}$ of the total number of torque values measured, a certain confidence level is achieved and the controller 20 continues with the analysis described below. Such threshold percentage $P_{Thresh1}$ can be 60%, 70%, 80%, 90%, 95%, 96%, 97%, 98%, or 99%, for example. As shown by block 226b, if the number of bone-engaging torque samples is less than such threshold percentage $P_{Thresh1}$, the controller 20 can halt further analysis and require that more torque samples be measured which are greater than or equal to the first threshold $T_{Thresh1}$. For example, in some variants, after block 226b, the method returns to block 210 for further analysis and value collection.

If the number of bone-engaging torque samples is greater than or equal to such threshold percentage $P_{Thresh1}$, the controller 20 carries out block 226c. Block 226c can facilitate determining whether the drill bit 200 has recently transitioned from the interior cancellous portion of the bone 202 to a second cortical portion of bone 202 (for example, has recently transitioned through point C in FIG. 8). In some embodiments, to "capture" or detect such transition, at block 226c, controller 20 compares a consecutive pair of torque values (e.g., from the third group of torque values) to determine whether a difference between such pair is greater than or equal to a fourth threshold, referred to herein as "StepDelta" or "$\Delta_{Step}$." If such difference is greater than or equal to $\Delta_{Step}$, this can demonstrate a large rate of change between consecutive torque values that is indicative of transitioning from a cancellous portion to a cortical portion of bone 202. $\Delta_{Step}$ can be determined based upon statistics of past torque values (for example, one or more torque values in the first, second, and/or third group). For example, $\Delta_{Step}$ can be equal to a second threshold percentage $P_{Thresh2}$ of the average of all the torque values measured at a given point in the analysis. The average torque value "$T_{Avg.}$" can be equal to the sum of all torque values previously measured, stored, and/or recorded divided by the number of bone-engaging torque samples (e.g., the number of torque samples that were greater than or equal to the first threshold $T_{Thresh1}$). In some embodiments, $T_{Avg.}$ does not include discarded torque values, such as those from block 222.

If a difference between a consecutive pair of torque values from the third group of torque samples is greater than or equal to $\Delta_{Step}$, this can indicate that there has been a significant rate of change of torque values between such consecutive torque values, which in turn can indicate that drill bit 200 has recently transitioned from cancellous bone to a second cortical portion of bone 202 (for example, through point C shown in FIG. 9). If this is true, controller 20 moves to block 226d, which is described in more detail below. For example, as discussed below, in some embodiments, if a difference between a consecutive pair of torque values from the third group of torque samples is greater than or equal to $\Delta_{Step}$, the controller 20 operates to stop or reduce the rotation of the drill bit 200 (e.g., if it is desirable to move to block 240 before the drill bit 200 breaches the bone 202). If such difference between a consecutive pair of torque values from the third group of torque samples is less than $\Delta_{Step}$, the controller 20 moves on to block 226e, which is further described below. The second threshold percentage $P_{Thresh2}$ can be 8%, 9%, 10%, 11%, 12%, 13%, 14%, or 15%, or any percentage within a range bounded by any of these percentages, although other values are possible.

At block 226e, controller 20 can analyze one or more torque values within the third group of samples to determine whether drill bit 200 is currently drilling through the second cortical portion of bone 202 (for example, between points C and D in FIG. 8). Conducting the step of block 226e after block 226c where block 226c yields a "No" (e.g., a difference between a consecutive pair of torque values from the third group of torque samples is less than $\Delta_{Step}$) can be advantageous where stopping rotation of drill bit 200 prior to breaching the bone 202 is desirable. For example, in some cases it may be difficult for two consecutive torque values in the third group to "capture" the cancellous-to-cortical transition point (for example, point C in FIG. 8) because such two torque values are measured at discrete time intervals (for example, every 10 ms). Such cancellous-to-cortical transition point may not "fall within" such two consecutive torque values/measurements. In these cases, providing an alternative method for detecting whether the drill bit 200 is close to breaching bone 202 (for example, is drilling through the second cortical portion between points C and D in FIG. 8) can be advantageous.

At block 226e, controller 20 compares a given (for example, current or most recent) torque value with a fifth threshold, referred to herein as "Torque$_A$" or "$T_A$." If such current (e.g., most recent) torque value is greater or equal to $T_A$, this can indicate that the drill bit 200 is currently drilling through the second portion of cortical bone. $T_A$ can be equal to the average torque value $T_{Avg.}$ plus the $\Delta_{Step}$ (both discussed previously). $T_A$ thus represents a high torque value relative to previously recorded (e.g., measured) torque values.

If a given (e.g., current) torque value is greater than or equal to $T_A$, controller 20 can move to block 226f to conduct an additional test as to whether the given torque value is close to the maximum torque value recorded (e.g., measured) so far, $T_{Max}$. More specifically, at block 226f, controller 20 can determine a difference between a current (e.g., recent) torque value and $T_{Max}$, and further determine whether such difference is greater than or equal to a sixth threshold $T_{Thresh6}$. In some embodiments, controller 20 determines whether an absolute value of the difference between a current torque value and $T_{Max}$ is greater than or equal to the sixth threshold $T_{Thresh6}$. The sixth threshold $T_{Thresh6}$ can be 0.00295 in-oz, 0.00296 in-oz, 0.00297 in-oz, 0.00298 in-oz, 0.00299 in-oz, 0.003 in-oz, 0.00301 in-oz, 0.00302 in-oz, 0.00303 in-oz, 0.00304 in-oz, or 0.00305 in-oz, or any range bounded by any combination of these values, or any value within a range bounded by any of these values, although other values are possible.

If controller 20 determines that a difference (or absolute value of a difference) between a current torque value and $T_{Max}$ is greater than or equal to the sixth threshold $T_{Thresh6}$, controller 20 moves to block 226d, which is discussed further below. Alternatively, if controller 20 determines that such difference (or absolute value of a difference) is less than the sixth threshold $T_{Thresh6}$, controller 20 moves to block 226g.

At block 226g, controller 20 can check whether an event was recorded according to block 224c (indicating that the drill bit 200 was drilling through the first cortical portion) and/or can check the results of the determination made at block 224d (whether the drill bit 200 actually drilled through the first cortical portion of bone). If the controller 20 previously determined that drill bit 200 drilled in or through the first cortical portion of bone 202, controller 20 can move from block 226g to block 226d, which is described further below. Block 226g can be advantageous because, even if controller 20 determines at block 226f that a current (e.g., recent) torque value is not close enough (e.g., within the sixth threshold $T_{Thresh6}$) to $T_{Max}$, so long as the controller 20 recognizes that the first cortical portion has already been drilled in or through, the current (e.g., recent) torque value is sufficiently high (as determined by block 226e) such that it indicates that the drill bit 200 is currently drilling through the second cortical portion of bone 202. Alternatively, if controller 20 analyzes the results of block 224d and determines that the first cortical portion of bone 202 was not drilled in or through (e.g., that block 224f was determined), controller 20 can continue to collect and analyze subsequent torque values and carry out one or more of blocks 226a-226g thereafter.

In some embodiments, when results of the determinations of block 226c and/or blocks 226e-226g lead to block 226d, that can indicate that the drill bit 200 is drilling through the second cortical portion of bone 202. In response, the controller 22 can communicate with the motor 12 to stop or reduce rotation of drill bit 200. For example, at block 226c, when the controller 20 determines that drill bit 200 has recently transitioned from cancellous bone to a second cortical portion of bone 202 (for example, through point C shown in FIG. 8), the controller 20 of surgical driver 100 can communicate with the power source 28 and/or the motor 12 to turn motor 12 off and/or stop or reduce rotation of drill bit 200 (e.g., the controller 20 can move on to block 240). As another example, when the controller 20 determines that the drill bit 200 is currently drilling through the second cortical portion of bone 202 at block 226e and either of block 226f or block 226 result in a "Yes," the controller 20 of surgical driver 100 can communicate with the power source 28 and/or the motor 12 to turn motor 12 off and/or stop or reduce rotation of drill bit 200 (e.g., the controller 20 can move on to block 240). Alternatively, in some embodiments, as shown in FIG. 12, at block 226d, controller 20 can conduct further analysis and/or measure additional torque values. For example, where it is desirable to stop or reduce rotation of drill bit 200 after (as opposed to before) breaching bone 202, controller 20 can measure additional torque values and/or conduct further analysis to detect when such breach occurs. Such analysis is described below with respect to FIG. 13.

Drill Bit Breach

Figure 13:
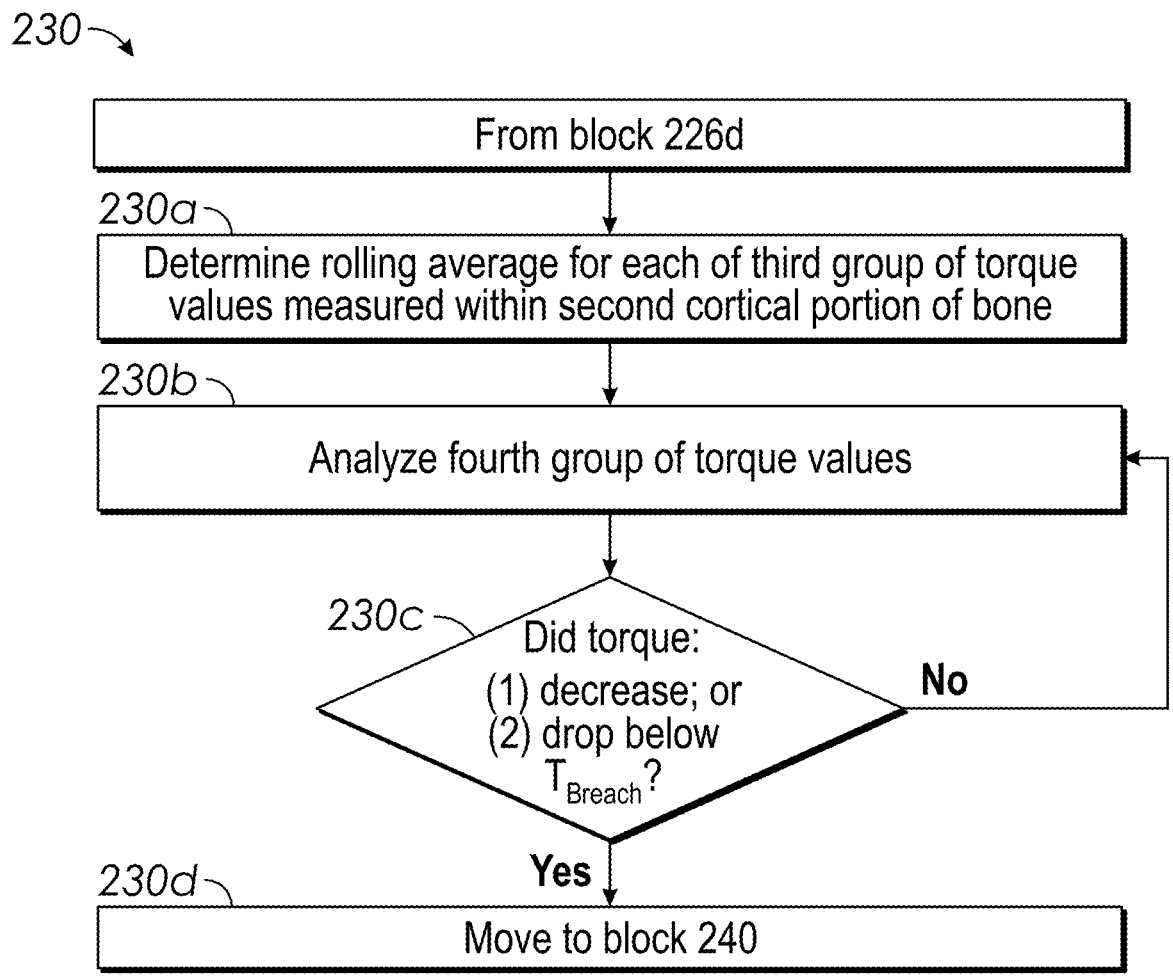
FIG. 13 illustrates additional features of the method of FIG. 10.

FIG. 13 illustrates block 230 in more detail. At a high level, block 230 can facilitate determining the location of the drill bit 200 with respect to a "breach" (exit) point or region of the second cortical portion of bone 202 as illustrated by point D in FIG. 8. To determine whether the drill bit 200 has breached through such point or region, it can be beneficial to compare current/recent measured torque values with previous torque values collected when drill bit 200 is drilling through the second cortical portion of bone 202. For example, as drill bit 200 is drilling through the second cortical portion, if measured torque values appear to decrease or fall below some threshold, this can be indicative that drill bit 200 has breached through bone 202 (for example, through point D in FIG. 8). In such cases, controller 20 can be configured to move to block 240 and, for example, reduce or stop rotation of drill bit 200.

With reference to block 230a, in some embodiments, for each torque value within the third group that results in a "Yes" for block 226c, block 226e and block 226f, or block 226g, controller 20 and/or processor 22 can determine a rolling average of such torque values. For example, if 5 torque samples from the third group of samples result in a "Yes" for block 226c, block 226e and block 226f, or block 226g, (representing drilling through the second cortical portion of bone 202), controller 20 and/or processor 22 can determine an average of these torque values, store such average, and update such average after each subsequent one of these 5 samples. Such average can advantageously be used as a breach threshold $T_{Breach}$ to determine whether the drill bit 200 has breached the bone 202. Controller 20 can carry out block 226 and block 230a for each of the third group of torque samples until all of the torque samples within the third group are measured. The precise number of torque values within the third group can be modified and can be dependent upon the sampling rate. For example, the third group of samples can include 15 torque samples, each measured at 10 ms intervals.

Some embodiments include collecting a fourth group of torque samples. In certain variants, after all of the torque samples in the third group have been analyzed according to block 226 and block 230a, controller 20 can measure and carry out analysis on a fourth group of torque samples at block 230b. As shown in FIG. 13, in some embodiments, at block 230b, controller 20 can compare one or more of the measured torque values in the fourth group to the breach threshold $T_{Breach}$. For example, at block 230b, controller 20 can determine whether a current measured torque value within the fourth group is less than the breach threshold $T_{Breach}$. As another example, at block 230b, controller 20 can determine whether two, consecutive torque values within the fourth group are less than the breach threshold $T_{Breach}$. As shown in block 230c, if one or more recent torque measurements within the fourth group are less than the breach threshold $T_{Breach}$, as shown by block 230d in FIG. 13, controller 20 can move to block 240 and can reduce or stop rotation of drill bit 200. As also shown in block 230c, if one or more recent torque measurements within the fourth group are not less than the breach threshold $T_{Breach}$, as shown by block 230e in FIG. 13, surgical driver 100 can continue drilling of drill bit 200 and controller 20 can continue to collect and analyze torque values according to block 230b.

In some cases, none of the torque samples in the third group registered that the drill bit 200 was drilling in/through the second cortical portion of bone 202. In such cases, with reference to FIG. 12, all of the torque values in the third group would have led to block 226b. As a result, when controller 20 begins collecting torque values within the fourth group, there will not be a breach threshold $T_{Breach}$ to compare such torque values with (e.g., $T_{Breach}=0$). In such cases, controller 20 can utilize the measured torque values from the fourth group to determine a rolling average and thus, breach threshold $T_{Breach}$, and thereafter compare subsequent torque measurements from the fourth group to such breach threshold $T_{Breach}$.

In some embodiments, controller 20 does not carry out block 230a. In such embodiments, controller 20 can analyze whether torque values are decreasing, and immediately upon making such determination, can move to block 240 to reduce or stop rotation of drill bit 200. For example, at block 230b, controller 20 can compare a current (e.g., recent) torque value with one or more past torque values and determine, at block 230c, whether the current (e.g., recent) torque value is less than such one or more past torque values. If the current (e.g., recent) torque value is less than such one or more past torque values, controller 20 can, as shown by block 230c, move to block 240. Alternatively, if a current (e.g., recent) torque value is not less than such one or more past torque values, surgical driver 100 can continue drilling of drill bit 200 and controller 20 can continue to collect and analyze torque values according to block 230b (see block 230e).

With reference to block 230c, if controller 20 determines that torque values are decreasing or that torque values are dropping below a threshold (e.g., $T_{Breach}$), this can indicate that drill bit 200 has breached bone 202. As discussed previously, such determination, and subsequent action taken according to block 240, can advantageously inhibit or prevent drilling through tissue adjacent or proximate to bone 202.

While the various steps and methods discussed above utilize the phrases "first group," "second group," "third group," and "fourth group," such phrases are not intended to be limiting. Such phrases are merely used to illustrate that one or more of the above-described blocks, steps, or processes measure and/or analyze one or more torque values to make various determinations that can advantageously help the controller 20 determine where drill bit 200 is with respect to the cross-section of bone 202. For example, use of the phrase "first group of torque samples/values" with respect to block 222 is meant to convey that a certain amount of initial torque values are discarded prior to measuring/analyzing additional torque values. Use of the phrase "second group of torque samples/values" with respect to block 224 and FIG. 11 is meant to convey that a certain amount of torque values (measured after the "first group") are measured/analyzed to determine whether the drill bit 200 is drilling in and/or has drilled through the first cortical portion of bone 202. Use of the phrase "third group of torque samples/values" with respect to block 226 and FIG. 12 is meant to convey that a certain amount of torque values (measured after the "second group") are measured/analyzed to determine whether the drill bit 200 is currently drilling in the second cortical portion of bone 202. Additionally, use of the phrase "fourth group of torque samples/values" with respect to block 230 and FIG. 13 is meant to convey that a certain amount of torque values (measured after the "third group") are measured/analyzed to determine where the drill bit 200 is with respect to the second cortical portion of bone and, more particularly, whether the drill bit 200 has drilled through the second cortical portion of bone 202. While precise amount of torque values within the first, second, third, and/or fourth group can vary, the controller 20 can carry out the above-described blocks, steps, and/or processes in order to determine the precise location of the drill bit 200 with respect to the cross-section of any bone 202.

The number of torque samples utilized and/or required in order to carry out the method/algorithm of FIGS. 9-13 can depend on factors including but not limited to the sampling rate, the thickness of bone, and the angle at which the drill bit 200 is with respect to an axis perpendicular to the bone surface. For example, if the angle of drill bit 200 with respect to an axis perpendicular to the bone surface is greater than 15 degrees, more than 25 torque samples may need to be taken in order to be able to carry out blocks 224 and/or 226.

While FIG. 8 illustrates an example cross-section of bone 202 and points A-D represent points where drill bit 200 may pass through, any of the devices, methods, systems, and/or algorithm discussed above are applicable where drill bit 200 drills through alternative points, regions, or angles with respect to bone 202 as illustrated in FIG. 8. For example, the method/algorithm described above with respect to FIGS. 9-13 is applicable where drill bit 200 drills through bone 202 at an angle that is non-perpendicular with respect to any point or surface along bone 202 and/or that is not aligned with a middle or center axis of bone 202. Regardless of the precise angle of drill bit 200 with respect to a point or surface of bone 202, the methods/algorithms described above with respect to FIGS. 9-12 can be utilized to determine whether a drill bit 200 is drilling through a second cortical portion of bone 202 in order to stop the motor 12 and inhibit or prevent damage to tissue proximate an exterior of the second cortical portion of the bone 202.

Certain Terminology

Conditional language used herein, such as, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. The term "and/or" means that "and" applies to some embodiments and "or" applies to some embodiments. Thus, A, B, and/or C is equivalent to A, B, and C written in one sentence and A, B, or C written in another sentence. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Terms relating to circular shapes as used herein, such as diameter or radius, should be understood not to require perfect circular structures, but rather should be applied to any suitable structure with a cross-sectional region that can be measured from side-to-side. Terms relating to shapes, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations. Likewise, shapes modified by the word "generally" (e.g., "generally cylindrical") can include reasonably close approximations of the stated shape. As used herein, any discussion of the "drill bit," such as the location of the drill bit relative to bone, can refer to the drill bit's tip (e.g., the distal-most end of the drill bit).

Some embodiments have been described in connection with the accompanying drawings. The figures are drawn to scale, but such scale should not be interpreted as limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

SUMMARY

Various surgical driver devices, systems, and methods have been disclosed in the context of aspects of certain embodiments, examples, and variations. The present disclosure extends beyond the specifically disclosed embodiments, examples, and variations to other alternative embodiments and/or uses of the invention, as well as obvious modifications and equivalents thereof. In addition, while a number of variations of the surgical driver have been shown and described in detail, other modifications, which are within the scope of this disclosure, will be readily apparent to those of skill in the art based upon this disclosure. Moreover, while certain examples have been discussed in the context of surgical drivers, the various inventions disclosed herein are not limited to use in surgical drivers. Indeed, the various inventions disclosed herein are contemplated for in use a variety of other types of devices and other environments.

Certain features have been described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Any of the steps and blocks can be adjusted or modified. Other or additional steps can be used. None of the steps or blocks described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

In summary, various embodiments and examples of torque-limiting surgical driver systems and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. Moreover, this disclosure expressly contemplates that various features and aspects of the disclosed embodiments can be combined with, or substituted for, one another. Accordingly, the scope of this disclosure should not be limited by the particular disclosed embodi- The following is claimed:

1. A torque-limiting surgical device comprising:
   a body comprising a handle that is configured to be grasped by a user;
   a motor positioned in the body;
   a drive head configured to be rotated by the motor and to drive a screw or drill bit; and
   a processor positioned in the body;
   wherein, under the control of the processor, the torque-limiting surgical device is configured to:
   apply torque to the screw or drill bit to drill into a bone;
   monitor current or voltage supplied to the motor;
   determine, from the current or voltage supplied to the motor, torque values applied to the screw or drill bit as the screw or drill bit drills through the bone;
   determine that a torque-limiting condition is satisfied, wherein the determining that the torque-limiting condition is satisfied comprises:
   determining that the screw or drill bit has drilled in or through a first cortical layer of the bone; and
   determining that the screw or drill bit has drilled through and exited a second cortical layer of the bone; and
   in response to determining that the torque-limiting condition is satisfied, stopping the application of torque to the screw or drill bit.

2. The torque-limiting surgical device of claim 1, wherein the torque-limiting surgical device is configured to determine whether the screw or drill bit has drilled in or through the first cortical layer of the bone by comparing a difference between a first pair of consecutive torque values to a first threshold.

3. The torque-limiting surgical device of claim 2, wherein the torque-limiting surgical device is further configured to determine at least one of:
   whether the screw or drill bit has drilled through an entry point of the second cortical layer of the bone; and
   whether the screw or drill bit is drilling in the second cortical layer of the bone.

4. The torque-limiting surgical device of claim 3, wherein the torque-limiting surgical device is configured to determine whether the screw or drill bit has drilled through the entry point of the second cortical layer of the bone by comparing a difference between a second pair of consecutive torque values to a second threshold, the second pair of consecutive torque values obtained after the first pair of consecutive torque values.

5. The torque-limiting surgical device of claim 4, wherein the second threshold is equal to a percentage of an average of a subset of all the determined torque values.

6. The torque-limiting surgical device of claim 5, wherein the subset of all of the determined torque values is equal to all of the determined torque values that are greater than or equal to a third threshold, wherein the third threshold is indicative of drilling through a material other than air.

7. The torque-limiting surgical device of claim 3, wherein the torque-limiting surgical device is configured to determine whether the screw or drill bit is drilling in the second cortical layer of the bone by comparing a difference between a current torque value and a maximum measured torque value to a second threshold.

8. The torque-limiting surgical device of claim 3, wherein, in response to a determination that the screw or drill bit has drilled through the entry point of the second cortical layer of the bone or a determination that the screw or drill bit is drilling in the second cortical layer of the bone, the torque-limiting surgical device is further configured to determine an average torque value, the average torque value representative of the torque values measured when the screw or drill bit is drilling in the second cortical layer of the bone.

9. The torque-limiting surgical device of claim 8, wherein the torque-limiting surgical device is further configured to determine a difference between a first torque value and the average torque value, the first torque value being a current torque value measured by the torque-limiting surgical device.

10. The torque-limiting surgical device of claim 9, wherein, the torque-limiting surgical device is configured to limit the amount of torque applied to the screw or drill bit in response to a determination that the first torque value is less than the average torque value.

11. The torque-limiting surgical device of claim 9, wherein the torque-limiting surgical device is further configured to:
    determine a difference between a second torque value and the average torque value, the second torque value measured prior to the first torque value; and
    limit the amount of torque applied to the screw or drill bit in response to a determination that both of the first and second torque values are less than the average torque value.

12. A method of controlling a torque-limiting device to limit the amount of torque applied to a screw or drill bit after breaching a bone, the torque-limiting device comprising a body with a handle, a motor positioned in the body, a drive head that is configured to drill a screw or drill bit and to be rotated by the motor so as to enable the screw or drill bit to drill into the bone, and a processor, wherein under the control of the processor the method comprises:
    driving the screw or drill bit into the bone, wherein the bone comprises a first cortical layer, a second cortical layer, and a cancellous layer in between the first and second cortical layers;
    detecting torque values when the screw or drill bit is drilling into the bone;
    determining whether the screw or drill bit has drilled in the first cortical layer of the bone;
    determining whether the screw or drill bit has drilled through and exited the second cortical layer of the bone; and
    in response to determining that the screw or drill bit has drilled through and exited the second cortical layer of the bone, stopping the driving of the screw or drill bit.

13. The method of claim 12, wherein the step of determining whether the screw or drill bit has drilled in the first cortical layer of the bone comprises comparing a difference between a first pair of consecutive torque values to a first threshold.

14. The method of claim 13, further comprising determining at least one of:
    whether the screw or drill bit has drilled through an entry point of the second cortical layer of the bone; and
    whether the screw or drill bit is drilling in the second cortical layer of the bone.

15. The method of claim 14, wherein, in response to a determination that the screw or drill bit has drilled through the entry point of the second cortical layer of the bone or a determination that the screw or drill bit is drilling in the second cortical layer of the bone, the method further comprises determining an average torque value, the average torque value representative of torque values measured when the screw or drill bit is drilling in the second cortical layer of the bone.

16. The method of claim 15, further comprising determining a difference between a first torque value and the average torque value, the first torque value being a current torque value measured by the torque-limiting surgical device.

17. The method of claim 16, further comprising limiting the amount of torque applied to the screw or drill bit in response to a determination that the first torque value is less than the average torque value.

* * * * *